US009795485B2

(12) United States Patent
Allain et al.

(10) Patent No.: US 9,795,485 B2
(45) Date of Patent: Oct. 24, 2017

(54) INTERSOMATIC CAGE, INTERVERTEBRAL PROSTHESIS, ANCHORING DEVICE AND IMPLANTATION INSTRUMENTS

(71) Applicant: LDR Medical, Troyes (FR)

(72) Inventors: Jerome Allain, Bagnolet (FR); Jean Lombard, Niort (FR); Jeff Phelps, North Richland Hills, TX (US); Pierce Nunley, Shreveport, LA (US); Charles Gordon, Tyler, TX (US); Vincent Leone, Manhasset, NY (US); Michael Hisey, Flower Mound, TX (US)

(73) Assignee: LDR Medical, Sainte-Savine (FR)

( * ) Notice: Subject to any disclaimer, the term of this patent is extended or adjusted under 35 U.S.C. 154(b) by 0 days.

(21) Appl. No.: 13/732,244

(22) Filed: Dec. 31, 2012

(65) Prior Publication Data
US 2014/0114413 A1 Apr. 24, 2014

Related U.S. Application Data

(63) Continuation of application No. 12/134,884, filed on Jun. 6, 2008, now Pat. No. 8,343,219.

(30) Foreign Application Priority Data

Jun. 8, 2007 (FR) ...................................... 07 04155

(51) Int. Cl.
*A61F 2/44* (2006.01)
*A61F 2/46* (2006.01)
(Continued)

(52) U.S. Cl.
CPC ...... *A61F 2/30749* (2013.01); *A61B 17/0642* (2013.01); *A61B 17/809* (2013.01);
(Continued)

(58) Field of Classification Search
CPC .................... A61B 17/809; A61F 2002/30517
(Continued)

(56) References Cited

U.S. PATENT DOCUMENTS 344,683 A * 6/1886 Sherer ........................... 119/786
1,025,596 A * 5/1912 Strawser ....................... 411/358
(Continued)

FOREIGN PATENT DOCUMENTS

DE 4327054 4/1995
EP 0667127 8/1995
(Continued)

OTHER PUBLICATIONS

English language translation of RU 2004218 C1, originally published on Dec. 15, 1993.*
(Continued)

*Primary Examiner* — David H Willse
(74) *Attorney, Agent, or Firm* — Lauff Law PLLC

(57) ABSTRACT

An intersomatic cage, an intervertebral prosthesis, an anchoring device and an instrument for implantation of the cage or the prosthesis and the anchoring device are provided. An intersomatic cage or an intervertebral prosthesis fit closely to the anchoring device, which includes a body of elongated shape on a longitudinal axis, of curved shape describing, along the longitudinal axis, an arc whose dimensions and radius of curvature are designed in such a manner that the anchoring device may be implanted in the vertebral plate of a vertebra by presenting its longitudinal axis substantially along the plane of the intervertebral space, where the anchoring device is inserted, by means of the instrument, through a slot located in at least one peripheral wall of the cage or on at least one plate of the intervertebral disc prosthesis to penetrate into at least one vertebral plate.

21 Claims, 11 Drawing Sheets

Figure 1A:
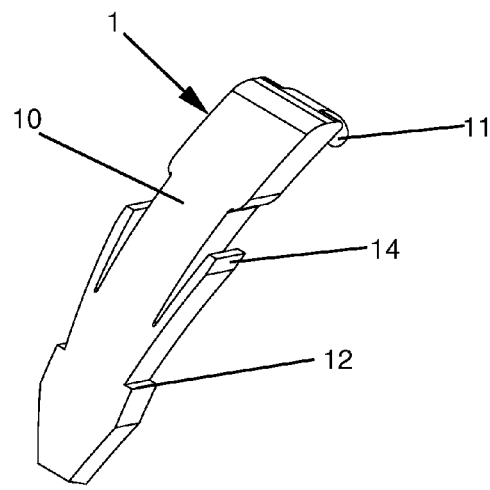

(51) Int. Cl.
*A61F 2/30* (2006.01)
*A61B 17/80* (2006.01)
*A61B 17/064* (2006.01)
*A61F 2/28* (2006.01)

(52) U.S. Cl.
CPC ............ *A61F 2/447* (2013.01); *A61F 2/4425* (2013.01); *A61F 2/4455* (2013.01); *A61F 2/4465* (2013.01); *A61F 2/4611* (2013.01); *A61F 2002/2835* (2013.01); *A61F 2002/302* (2013.01); *A61F 2002/305* (2013.01); *A61F 2002/30112* (2013.01); *A61F 2002/30116* (2013.01); *A61F 2002/30331* (2013.01); *A61F 2002/30517* (2013.01); *A61F 2002/30576* (2013.01); *A61F 2002/30579* (2013.01); *A61F 2002/30601* (2013.01); *A61F 2002/30622* (2013.01); *A61F 2002/30662* (2013.01); *A61F 2002/30777* (2013.01); *A61F 2002/30782* (2013.01); *A61F 2002/30879* (2013.01); *A61F 2002/30904* (2013.01); *A61F 2002/443* (2013.01); *A61F 2002/448* (2013.01); *A61F 2002/4475* (2013.01); *A61F 2002/4629* (2013.01); *A61F 2002/4681* (2013.01); *A61F 2220/0025* (2013.01); *A61F 2220/0033* (2013.01); *A61F 2230/0004* (2013.01); *A61F 2230/0006* (2013.01); *A61F 2230/0065* (2013.01)

(58) Field of Classification Search
USPC ..... 411/356, 358, 451.3, 456, 459, 468, 472
See application file for complete search history.

(56) References Cited

U.S. PATENT DOCUMENTS

| | | | |
|---|---|---|---|
| 1,121,484 A * | 12/1914 | Crites | 411/358 |
| 3,875,595 A | 4/1975 | Froning | |
| 3,948,262 A | 4/1976 | Zaffaroni | |
| 4,349,921 A | 9/1982 | Kuntz | |
| 4,507,115 A | 3/1985 | Kambara et al. | |
| 4,834,757 A | 5/1989 | Brantigan | |
| 4,863,476 A | 9/1989 | Shepperd | |
| 4,892,545 A | 1/1990 | Day et al. | |
| 5,326,205 A | 7/1994 | Anspach, Jr. et al. | |
| 5,443,514 A | 8/1995 | Steffee | |
| 5,501,695 A | 3/1996 | Anspach, Jr. et al. | |
| 5,658,335 A | 8/1997 | Allen | |
| 5,683,394 A | 11/1997 | Rinner | |
| 5,810,820 A | 9/1998 | Santori et al. | |
| 5,849,004 A | 12/1998 | Bramlet | |
| 5,888,228 A | 3/1999 | Knothe et al. | |
| 5,976,139 A | 11/1999 | Bramlet | |
| 6,183,474 B1 | 2/2001 | Bramlet et al. | |
| 6,210,442 B1 | 4/2001 | Wing et al. | |
| 6,231,610 B1 | 5/2001 | Geisler | |
| 6,258,089 B1 | 7/2001 | Campbell et al. | |
| 6,383,186 B1 | 5/2002 | Michelson | |
| 6,419,706 B1 | 7/2002 | Graf | |
| 6,447,546 B1 * | 9/2002 | Bramlet et al. | 623/17.16 |
| 6,527,803 B1 | 3/2003 | Crozet et al. | |
| 6,540,753 B2 | 4/2003 | Cohen | |
| 6,620,163 B1 | 9/2003 | Michelson | |
| 6,695,846 B2 | 2/2004 | Richelsoph et al. | |
| 6,712,818 B1 | 3/2004 | Michelson | |
| 6,770,096 B2 * | 8/2004 | Bolger et al. | 623/17.16 |
| 7,051,610 B2 | 5/2006 | Stoianovici et al. | |
| 7,137,984 B2 | 11/2006 | Michelson | |
| 7,204,852 B2 | 4/2007 | Marnay et al. | |
| 7,235,082 B2 | 6/2007 | Bartish et al. | |
| 7,255,698 B2 | 8/2007 | Michelson | |
| 7,303,583 B1 | 12/2007 | Schar et al. | |
| 7,455,684 B2 | 11/2008 | Gradel et al. | |
| 7,473,276 B2 | 1/2009 | Aebi et al. | |
| 7,563,284 B2 | 7/2009 | Coppes et al. | |
| 7,563,286 B2 | 7/2009 | Gerber et al. | |
| 7,611,538 B2 | 11/2009 | Belliard et al. | |
| 7,637,953 B2 | 12/2009 | Branch et al. | |
| 7,744,602 B2 | 6/2010 | Teeny et al. | |
| 7,771,478 B2 | 8/2010 | Navarro et al. | |
| 7,846,188 B2 | 12/2010 | Moskowitz et al. | |
| 7,905,886 B1 | 3/2011 | Curran et al. | |
| 8,080,062 B2 | 12/2011 | Armstrong et al. | |
| 8,257,443 B2 | 9/2012 | Kamran et al. | |
| 8,267,999 B2 | 9/2012 | Beaurain et al. | |
| 8,303,663 B2 | 11/2012 | Jimenez et al. | |
| 8,313,528 B1 | 11/2012 | Wensel | |
| 8,323,345 B2 | 12/2012 | Sledge | |
| 8,343,197 B2 | 1/2013 | Gonzalez-Hernandez | |
| 8,343,219 B2 | 1/2013 | Allain et al. | |
| 8,349,015 B2 | 1/2013 | Bae et al. | |
| 8,535,352 B2 | 9/2013 | Altarac et al. | |
| 8,545,563 B2 | 10/2013 | Brun et al. | |
| 8,617,245 B2 | 12/2013 | Brett | |
| 8,696,681 B2 | 4/2014 | Harris et al. | |
| 8,979,932 B2 | 3/2015 | Rashbaum et al. | |
| 9,044,337 B2 | 6/2015 | Dinville et al. | |
| 2002/0059938 A1 | 5/2002 | Fogarty et al. | |
| 2002/0070565 A1 | 6/2002 | Szapucki et al. | |
| 2003/0149484 A1 | 8/2003 | Michelson | |
| 2003/0191531 A1 | 10/2003 | Berry et al. | |
| 2004/0143332 A1 | 7/2004 | Krueger et al. | |
| 2005/0027362 A1 | 2/2005 | Williams et al. | |
| 2005/0065611 A1 | 3/2005 | Huppert et al. | |
| 2005/0143733 A1 * | 6/2005 | Petit | 606/60 |
| 2005/0283236 A1 | 12/2005 | Razian | |
| 2006/0085071 A1 | 4/2006 | Lechmann et al. | |
| 2006/0121084 A1 * | 6/2006 | Borden et al. | 424/426 |
| 2006/0142863 A1 | 6/2006 | Fraser et al. | |
| 2006/0178745 A1 | 8/2006 | Bartish, Jr. et al. | |
| 2006/0241621 A1 | 10/2006 | Moskowitz et al. | |
| 2006/0241761 A1 | 10/2006 | Gately | |
| 2006/0276899 A1 | 12/2006 | Zipnick et al. | |
| 2007/0049943 A1 | 3/2007 | Moskowitz et al. | |
| 2007/0093850 A1 | 4/2007 | Harris et al. | |
| 2007/0106388 A1 | 5/2007 | Michelson | |
| 2007/0142843 A1 | 6/2007 | Dye | |
| 2007/0162128 A1 | 7/2007 | DeRidder et al. | |
| 2007/0208345 A1 | 9/2007 | Marnay et al. | |
| 2007/0270960 A1 | 11/2007 | Bonin et al. | |
| 2008/0033432 A1 | 2/2008 | McGraw et al. | |
| 2008/0132949 A1 | 6/2008 | Aferzon et al. | |
| 2008/0177306 A1 | 7/2008 | Lamborne et al. | |
| 2009/0112271 A1 | 4/2009 | Moskowitz et al. | |
| 2009/0216331 A1 | 8/2009 | Grotz et al. | |
| 2010/0016903 A1 | 1/2010 | Matityahu et al. | |
| 2010/0016974 A1 | 1/2010 | Janowski et al. | |
| 2010/0050276 A1 | 2/2010 | DePaepe | |
| 2010/0298941 A1 | 11/2010 | Hes et al. | |
| 2011/0112587 A1 | 5/2011 | Patel et al. | |
| 2011/0178599 A1 | 7/2011 | Brett | |
| 2012/0022654 A1 | 1/2012 | Farris et al. | |
| 2012/0078371 A1 | 3/2012 | Gamache et al. | |
| 2012/0197404 A1 | 8/2012 | Brun et al. | |
| 2013/0150968 A1 | 6/2013 | Dinville et al. | |
| 2013/0166029 A1 | 6/2013 | Dinville et al. | |
| 2015/0051702 A1 | 2/2015 | Chataigner et al. | |

FOREIGN PATENT DOCUMENTS

| | | |
|---|---|---|
| FR | 2823095 | 10/2002 |
| FR | 2987256 | 8/2013 |
| FR | 3005569 | 11/2014 |
| FR | 3016793 | 7/2015 |
| RU | 2004218 | 12/1993 |
| WO | WO03039400 | 5/2003 |
| WO | WO2004080356 | 9/2004 |
| WO | WO2006102269 | 9/2006 |
| WO | WO2008044057 | 4/2008 |
| WO | WO2010090801 | 8/2010 |
| WO | WO2011129973 | 10/2011 |

(56) References Cited

FOREIGN PATENT DOCUMENTS

| WO | WO2013124453 | 8/2013 |
|----|--------------|--------|
| WO | WO2014184367 | 11/2014 |
| WO | WO2015114122 | 8/2015 |

OTHER PUBLICATIONS

U.S. Appl. No. 09/635,436, filed Aug. 11, 2000, Bramlet, Dale G. et al., Apparatus and Method for Fusing Opposing Spinal Vertebrae.
U.S. Appl. No. 10/060,862, filed Jan. 30, 2002, Gau, Michel, Intervertebral nucleus prosthesis and surgical procedure for implanting the same.
U.S. Appl. No. 10/276,712, filed Mar. 26, 2003, Huppert, Jean, Intersomatic cage with unified grafts.
U.S. Appl. No. 10/473,999, filed Apr. 12, 2004, Beaurain, Jaques et al., Spinal Osteosynthesis Device and Preparation Method.
U.S. Appl. No. 10/476,565, filed Jun. 8, 2004, Beaurain, Jaques et al., Intervertebral Disc Prosthesis and Fitting Tools.
U.S. Appl. No. 10/483,563, filed May 21, 2004, Louis, Christian et al., Vertebral Cage Device With Modular Fixation.
U.S. Appl. No. 10/492,753, filed Aug. 9, 2004, Delecrin, Joel et al., Progressive approach osteosynthesis device and preassembly method.
U.S. Appl. No. 10/492,827, filed Jul. 15, 2004, Delecrin, Joel et al., Plate for osteosynthesis device and method for preassembling such device.
U.S. Appl. No. 10/494,418, filed Jul. 22, 2004, Huppert, Jean et al., Osseous anchoring device for a prosthesis.
U.S. Appl. No. 10/498,234, filed Dec. 7, 2004, Beaurain, Jaques et al., Implant for Osseous Anchoring with Polyaxial Head.
U.S. Appl. No. 10/533,846, filed Nov. 11, 2005, Beaurain, Jaques et al., Intervertebral Disk Prosthesis.
U.S. Appl. No. 10/570,080, filed Jun. 9, 2006, Renaud, Christian et al., Osseous anchoring implant with a polyaxial head and method for installing the implant.
U.S. Appl. No. 10/575,065, filed May 30, 2006, Mangione, Paolo, Device and method for sectioning a vertebral lamina.
U.S. Appl. No. 11/051,710, filed Feb. 4, 2005, Hovorka, Istvan et al., Intervertebral Disc Prosthesis.
U.S. Appl. No, 11/098,266, filed Apr. 4, 2005, Zeegers, M. Willem, Intervertebral Disc Prosthesis.
U.S. Appl. No. 11/109,276, filed Apr. 18, 2005, Zeegers, M. Willem, Intervertebral Disc Prosthesis.
U.S. Appl. No. 11/180,868, filed Jul. 13, 2005, Dinville, Herve, Instrumentation and Methods for Inserting an Intervertebral Disc Prosthesis.
U.S. Appl. No. 11/341,007, filed Jan. 27, 2006, Rashbaum, Ralph et al., Interbertebral Disc Prosthesis.
U.S. Appl. No. 11/362,253, filed Feb. 24, 2006, Rashbaum, Ralph et al., Intervertebral Disc Prosthesis and Instrumentation for Insertion of the Prosthesis Between the Vertebrae.
U.S. Appl. No. 11/378,165, filed Mar. 17, 2006, Davis, Reginald James et al., Transforanimal intersomatic cage for an intervertebral fusion graft and an instrument for implanting the cage.
U.S. Appl. No. 11/390,711, filed Mar. 27, 2006, Gau, Michel, Intervertebral nucleus prosthesis and surgical procedure for implanting the same.
U.S. Appl. No. 11/676,237, filed Feb. 16, 2007, Jodaitis, Alexandre et al., Intervertebral disc prosthesis insertion assemblies.
U.S. Appl. No. 11/767,386, filed Jun. 22, 2007, Huppert, Jean, Intersomatic cage with unified grafts.
U.S. Appl. No. 11/874,144, filed Oct. 17, 2007, Vila, Thierry et al., Modular intervertebral prosthesis.
U.S. Appl. No. 11/958,285, filed Dec. 17, 2007, Cho, Paul et al., Vertebral Support Device.
U.S. Appl. No. 12/025,677, filed Feb. 4, 2008, Beaurain, Jaques et al., Intervertebral disc prosthesis surgical methods, and fitting tools.
U.S. Appl. No. 12/134,884, filed Jun. 6, 2008, Allain, Jerome et al., Intersomatic cage, intervertebral prosthesis, anchoring device and implantation instruments.
U.S. Appl. No. 12/172,074, filed Jul. 11, 2008, Cho, Paul, Transverse spinal linking device and system.
U.S. Appl. No. 12/279,664, filed Apr. 22, 2009, Davis, Reginald James et al., Transforaminal intersomatic cage for an intervertebral fusion graft and an instrument for implanting the cage.
U.S. Appl. No. 12/360,050, filed Jan. 26, 2009, Zeegers, M. Willem, Intervertebral Disc Prosthesis.
U.S. Appl. No. 12/391,086, filed Feb. 23, 2009, Zeegers, M. Willem, Intervertebral Disc Prosthesis.
U.S. Appl. No. 12/409,327, filed Mar. 23, 2009, Beaurain, Jaques et al., Spinal Osteosynthesis Device and Preparation Method.
U.S. Appl. No. 12/424,364, filed Apr. 15, 2009, Beaurain, Jaques et al., Intervertebral disc prosthesis.
U.S. Appl. No. 12/430,768, filed Apr. 27, 2009, Louis, Christian et al., Vertebral Cage Device with Modular Fixation.
U.S. Appl. No. 12/435,955, filed May 5, 2009, Dinville, Herve, Instrumentation and Methods for Inserting an Intervertebral Disc Prosthesis.
U.S. Appl. No. 12/527,373, filed Mar. 19, 2010, Jodaitis, Alexandre et al., Intervertebral disc prosthesis insertion assemblies.
U.S. Appl. No. 12/884,664, filed Sep. 17, 2010, Brett, Darrell C., Intervertebral implant having extendable bone fixation members.
U.S. Appl. No. 12/955,898, filed Nov. 29, 2010. Rashbaum, Ralph et al., Intervertebral Disc Prosthesis.
U.S. Appl. No. 13/158,761, filed Jun. 13, 2011, Dinville, Herve et al., Instruments and Methods for Removing Fixation Devices from Intervertebral Implants.
U.S. Appl. No. 13/215,123, filed Aug. 22, 2011, Zeegers, M. Willem, Intervertebral Disc Prosthesis.
U.S. Appl. No. 13/369,650, filed Feb. 9, 2012, Dinville, Hervé et al., Interspinous Implant and Implantation Instrument.
U.S. Appl. No. 13/438,352, filed Apr. 3, 2012, Louis, Christian et al., Vertebral Cage Device With Modular Fixation.
U.S. Appl. No. 13/454,927, filed Apr. 24, 2012, Delecrin, Joel et al., Plate for osteosynthesis device and method of preassembling such device.
U.S. Appl. No. 13/520,041, filed Nov. 26, 2012, Dinville, Hervé et al., Anchoring Device and System for an Intervertebral Implant, Intervertebral Implant and Implantation Instrument.
U.S. Appl. No. 13/538,078, filed Jun. 29, 2012, Dinville, Hervé et al., Anchoring Device and System for an Intervertebral Implant, Intervertebral Implant and Implantation Instrument.
U.S. Appl. No. 13/585,063, filed Aug. 14, 2012, Davis, Reginald James et al., Transforaminal intersomatic cage for an intervertebral fusion graft and an instrument for implanting the cage.
U.S. Appl. No. 13/603,043, filed Sep. 4, 2012, Zeegers, M. Willem, Intervertebral Disc Prosthesis.
U.S. Appl. No. 13/616,448, filed Sep. 14, 2012, Beaurain, Jacques et al., Intervertebral Disk Prosthesis.
U.S. Appl. No. 13/620,797, filed Sep. 15, 2012, Rashbaum, Ralph et al., Intervertebral Disc Prosthesis and Instrumentation for Insertion of the Prosthesis Between the Vertebrae.
U.S. Appl. No. 13/732,244, filed Dec. 31, 2012, Allain, Jerome et al., Intersomatic cage, intervertebral prosthesis, anchoring device, and implantation instruments.
U.S. Appl. No. 13/774,547, filed Feb. 22, 2013, Chataigner, Hervé et al., Anchoring device and system for an intervertebral implant, intervertebral implant and implantation instrument.
U.S. Appl. No. 13/854,808, filed Apr. 1, 2013, Davis, Reginald James et al., Transforanimal intersomatic cage for an intervertebral fusion graft and an instrument for implanting the cage.
U.S. Appl. No. 13/873,190, filed Apr. 29, 2013, Beaurain, Jacques et al., Spinal Osteosynthesis Device and Preparation Method.
U.S. Appl. No. 13/892,933, filed May 13, 2013, Dinville, Herve, Instrumentation and Methods for Inserting an Intervertebral Disc Prosthesis.
U.S. Appl. No. 13/919,704, filed Jun. 17, 2013, Jodaitis, Alexandre et al., Prosthesis for Spinal Treatment.
U.S. Appl. No. 14/064,434, filed Oct. 28, 2013, Brett, Darrell C., Intervertebral implant having extendable bone fixation members.

(56) References Cited

OTHER PUBLICATIONS

U.S. Appl. No. 14/130,286, filed Jul. 3, 2014, Dinville, Hervé et al., Interspinous Implant and Implantation Instrument.
U.S. Appl. No. 14/149,357, filed Jan. 7, 2014, Huppert, Jean, Intersomatic cage with unified grafts.
U.S. Appl. No. 14/159,161, filed Jan. 20, 2014, Vila, Thierry et al., Nucleus Prostheses.
U.S. Appl. No. 14/242,177, filed Apr. 1, 2014, Jodaitis, Alexandre et al., Intervertebral disc prosthesis insertion assemblies.
U.S. Appl. No. 14/246,442, filed Apr. 7, 2014, Dinville, Hervé et al., Vertebral implant, vertebral fastening device of the implant and implant instrumentation.
U.S. Appl. No. 14/252,754, filed Apr. 14, 2014, Dinville, Hervé et al., Interspinous Implant and Implantation Instrument.
U.S. Appl. No. 14/252,852, filed Apr. 15, 2014, Chataigner, Hervé et al., Anchoring device for a spinal implant, spinal implant and implantation instrumentation.
U.S. Appl. No. 14/306,785, filed Jun. 17, 2014, Beaurain, Jacques et al., Intervertebral Disk Prosthesis.
U.S. Appl. No. 14/325,317, filed Jul. 7, 2014, Steib, Jean-Paul, Intervertebral Disc Prosthesis and Instrumentation for Insertion of the Prosthesis Between the Vertebrae.
U.S. Appl. No. 14/380,714, filed Aug. 23, 2014, Chataigner, Hervé et al., Anchoring device and system for an intervertebral implant, intervertebral implant and implantation instrument.
U.S. Appl. No. 14/460,536, filed Aug. 15, 2014, Kim, Seo-Kon et al., Cage Having Spike.
U.S. Appl. No. 14/497,321, filed Sep. 26, 2014, Renaud, Christian et al., Osseous anchoring implant with a polyaxial head and method for installin the implant.
U.S. Appl. No. 14/513,818, filed Oct. 14, 2014, Hovorka, Istvan et al., Intervertebral Disc Prosthesis.
U.S. Appl. No. 14/584,674, filed Dec. 29, 2014, Delecrin, Joel et al., Plate for Osteosynthesis device and method of preassembling such device.
U.S. Appl. No. 14/594,770, filed Jan. 12, 2015, Brett, Darrell C., Intervertebral Implant Having Extendable Bone Fixation Members.
U.S. Appl. No. 14/638,746, filed Mar. 4, 2015, Ameil, Marc et al., Vertebral implant, device for vertebral attachment of the implant and instrumentation for implantation thereof.
U.S. Appl. No. 14/642,696, filed Mar. 9, 2015, Zeegers, M. Willem, Intervertebral Disc Prosthesis.
U.S. Appl. No. 14/642,672, filed Mar. 10, 2015, Cho, Paul et al., Vertebral Support Device.
U.S. Appl. No. 14/659,587, filed Mar. 16, 2015, Rashbaum, Ralph et al., Intervertebral Implant Having Extendable Bone Fixation Members.
U.S. Appl. No. 14/721,818, filed May 26, 2015, Chataigner, Hervé et al., Anchoring device and system for an intervertebral implant, intervertebral implant and implantation instrument.
U.S. Appl. No. 14/726,557, filed May 31, 2015, Zeegers, M. Willem, Intervertebral Disc Prosthesis.
U.S. Appl. No. 14/726,558, filed May 31, 2015, Dinville, Hervé et al., Anchoring Device and System for an Intervertebral Implant and Implantation Instrument.
U.S. Appl. No 14/798,900, filed Jul. 14, 2015, Louis, Christian et al., Vertebral Cage Device With Modular Fixation.
U.S. Appl. No. 14/815,900, filed Jul. 31, 2015, Lavigne, Christophe et al., Bone Implants.
U.S. Appl. No. 14/827,297, filed Aug. 15, 2015, Stewart, Will et al., Devices, Methods, and Systems to Implant and Secure a Fusion Cage or Intervertebral Prosthesis for Spinal Treatment.
U.S. Appl. No. 14/891,322, filed Nov. 13, 2015, Dinville, Herve et al., Vertebral implant, vertebral fastening device of the implant and implant instrumentation.
U.S. Appl. No. 14/931,007, filed Nov. 3, 2015, Dinville, Herve et al., Instruments and Methods for Removing Fixation Devices from Intervertebral Implants.
U.S. Appl. No. 15/012,815, filed Feb. 1, 2016, Dinville, Herve, Instrumentation and Methods for Inserting an Intervertebral Disc Prosthesis.
U.S. Appl. No. 15/049,934, filed Feb. 22, 2016, Beaurain, Jacques et al., Intervertebral Disk Prosthesis.
U.S. Appl. No. 15/049,995, filed Feb. 22, 2016, Steib, Jean-Paul, Intervertebral Disc Prosthesis and Instrumentation for Insertion of the Prosthesis Between the Vertebrae.
U.S. Appl. No. 15/144,638, filed May 2, 2016, Vertebral implant and insert for vertebral implant.
U.S. Appl. No. 15/145,413, filed May 3, 2016, Dinville, Hervé et al., Interspinous Implant and Implantation Instrument.
U.S. Appl. No. 15/145,431, filed May 3, 2016, Beaurain, Jacques et al., Implant for Osseous Anchoring with Polyaxial Head.
U.S. Appl. No. 61/243,297, filed Sep. 17, 2009, Brett, Darrell C., Intervertebral Fusion Cage with Retractable-Extrudable Pins.
U.S. Appl. No. 61/260,364, filed Nov. 11, 2009, Brett, Darrell C., Intervertebral Fusion Cage with Retractable-Extrudable Pins.
National Institute of Industrial Property (France); Search Report in Fench Pub. No. FR2987256, App. No. FR1251733; Dec. 5, 2012; National Institute of Industrial Property (France); France; all pages.
World Intellectual Property Organization; International Search Report and Written Opinion of the International Searching Authority for International App. No. PCT/EP2013/053622, PCT Pub'n. No. WO2013124453; May 29, 2013; WIPO; Geneva, Switzerland; all pages.
U.S. Patent & Trademark Office; Office Action in U.S. Appl. No. 13/520,041; Mar. 20, 2014; USPTO; Alexandria, Virgina; All Pages.
U.S. Patent & Trademark Office; Office Action in U.S. Appl. No. 13/538,078; May 12, 2014; USPTO; Alexandria, Virgina; All Pages.
U.S. Patent & Trademark Office; Examiner's Interview Summary in U.S. Appl. No. 13/774,547; Jul. 3, 2014; USPTO; Alexandria, Virgina; All Pages.
World Intellectual Property Organization; International Preliminary Report on Patentability for International App. No. PCT/EP2013/053622, PCT Pub'n. No. WO 2013/124453; Jul. 11, 2014; WIPO; Geneva, Switzerland; all pages.
U.S. Patent & Trademark Office; Office Action in U.S. Appl. No. 13/438,352; Aug. 14, 2014; USPTO; Alexandria, Virgina; All Pages.
U.S. Patent & Trademark Office; Office Action in U.S. Appl. No. 13/520,041; Oct. 6, 2014; USPTO; Alexandria, Virgina; All Pages.
U.S. Patent & Trademark Office; Office Action in U.S. Appl. No. 13/585,063; Nov. 6, 2014; USPTO; Alexandria, Virgina; All Pages.
LDR Medical, by its attorneys; Reply to Office Action in U.S. Appl. No. 13/774,547; Feb. 2, 2015; USPTO; Alexandria, Virgina; All Pages.
U.S. Patent & Trademark Office; Office Action in U.S. Appl. No. 13/585,063; Feb. 11, 2015; USPTO; Alexandria, Virgina; All Pages.
U.S. Patent & Trademark Office; Office Action in U.S. Appl. No. 13/520,041; Apr. 10, 2015; USPTO; Alexandria, Virgina; All Pages.
U.S. Patent & Trademark Office; Office Action in U.S. Appl. No. 14/721,818; Sep. 24, 2015; USPTO; Alexandria, Virgina; All Pages.
U.S. Patent & Trademark Office; Office Action in U.S. Appl. No. 13/585,063; Nov. 4, 2015; USPTO; Alexandria, Virgina; All Pages.
U.S. Patent & Trademark Office; Office Action in U.S. Appl. No. 14/721,818; Feb. 1, 2016; USPTO; Alexandria, Virgina; All Pages.
World Intellectual Property Organization; International Search Report and Written Opinon of the International Searching Authority for PCT Pub'n. No. WO2006120505, App. No. PCT/IB2005/004093; Aug. 31, 2006; WIPO; Geneva, Switzerland; all pages.
European Patent Office; search report in Application No. 10185004, Pub. No. EP2327375; Apr. 6, 2011; European Patent Office; Munich, Germany; All Pages.
Japan Patent Office; Office Action for Pub'n. No. JP2009532075, Application No. JP20080554874; Nov. 4, 2011; Japan Patent Office; Tokyo, Japan; all pages.
European Patent Office; Office action in Application No. 11165170, Pub. No. EP2363080; May 15, 2012; European Patent Office; Munich, Germany; All Pages.
U.S. Patent & Trademark Office; Office Action in U.S. Appl. No. 12/955,898; Jan. 10, 2013; USPTO; Alexandria, Virgina; All Pages.
U.S. Patent & Trademark Office; Office Action in U.S. Appl. No. 13/603,043; Apr. 9, 2013; USPTO; Alexandria, Virgina; All Pages.

(56) References Cited

OTHER PUBLICATIONS

U.S. Patent & Trademark Office; Office Action in U.S. Appl. No. 13/616,448; Aug. 22, 2013; USPTO; Alexandria, Virgina; All Pages.
European Patent Office; search report in Application No. 13170071, Pub. No. EP2633835; Oct. 1, 2013; European Patent Office; Munich, Germany; All Pages.
U.S. Patent & Trademark Office; Office Action in U.S. Appl. No. 13/603,043; Nov. 21, 2013; USPTO; Alexandria, Virgina; All Pages.
U.S. Patent & Trademark Office; Office Action in U.S. Appl. No. 12/955,898; Mar. 3, 2014; USPTO; Alexandria, Virgina; All Pages.
U.S. Patent & Trademark Office; Office Action in U.S. Appl. No. 13/603,043; Jul. 24, 2014; USPTO; Alexandria, Virgina; All Pages.
U.S. Patent & Trademark Office; Office Action in U.S. Appl. No. 14/306,785; Oct. 22, 2014; USPTO; Alexandria, Virgina; All Pages.
U.S. Patent & Trademark Office; Office Action in U.S. Appl. No. 14/659,587; Apr. 16, 2015; USPTO; Alexandria, Virgina; All Pages.
U.S. Patent & Trademark Office; Office Action in U.S. Appl. No. 14/306,785; Jun. 22, 2015; USPTO; Alexandria, Virgina; All Pages.
U.S. Patent & Trademark Office; Office Action in U.S. Appl. No. 14/726,557; Dec. 30, 2015; USPTO; Alexandria, Virgina; All Pages.
U.S. Patent & Trademark Office; Office Action in U.S. Appl. No. 14/659,587; Jan. 28, 2016; USPTO; Alexandria, Virgina; All Pages.
World Intellectual Property Organization; International Search Report and Written Opinion of the International Searching Authority for International App. No. WO2011035126, PCT Pub'n. No. PCT/US2010/049287; Jan. 11, 2011; WIPO; Geneva, Switzerland; all pages.
World Intellectual Property Organization; International Preliminary Report on Patentability for International App. No. WO2011035126, PCT Pub'n. No. PCT/US2010/049287; Mar. 20, 2012; WIPO; Geneva, Switzerland; all pages.
U.S. Patent & Trademark Office; Office Action in U.S. Appl. No. 12/884,664; Sep. 26, 2012; USPTO; Alexandria, Virgina; All Pages.
U.S. Patent & Trademark Office; Office Action in U.S. Appl. No. 13/158,761; Oct. 17, 2012; USPTO; Alexandria, Virgina; All Pages.
U.S. Patent & Trademark Office; Examiner's Interview Summary in U.S. Appl. No. 13/158,761; Oct. 31, 2012; USPTO; Alexandria, Virgina; All Pages.
U.S. Patent & Trademark Office; Examiner Interview Summary in U.S. Appl. No. 12/884,664; Dec. 18, 2012; USPTO; Alexandria, Virgina; All Pages.
U.S. Patent & Trademark Office; Office Action in U.S. Appl. No. 12/884,664; Jan. 15, 2013; USPTO; Alexandria, Virgina; All Pages.
U.S. Patent & Trademark Office; Office Action in U.S. Appl. No. 13/158,761; Feb. 28, 2013; USPTO; Alexandria, Virgina; All Pages.
U.S. Patent & Trademark Office; Examiner's Interview Summary in U.S. Appl. No. 13/158,761; Aug. 1, 2013; USPTO; Alexandria, Virgina; All Pages.
U.S. Patent & Trademark Office; Office Action in U.S. Appl. No. 13/158,761; Aug. 14, 2013; USPTO; Alexandria, Virgina; All Pages.
U.S. Patent & Trademark Office; Office Action in U.S. Appl. No. 14/064,434; Jan. 13, 2014; USPTO; Alexandria, Virgina; All Pages.
National Institute of Industrial Property (France); Search Report in Fench Pub. No. FR3005569, App. No. FR1354421; Feb. 12, 2014; National Institute of Industrial Property (France); France; all pages.
U.S. Patent & Trademark Office; Office Action in U.S. Appl. No. 14/064,434; May 5, 2014; USPTO; Alexandria, Virgina; All Pages.
World Intellectual Property Organization; International Search Report for International App. No. WO2014184367, PCT Pub'n. No. PCT/EP2014/060135; Aug. 26, 2014; WIPO; Geneva, Switzerland; all pages.
National Institute of Industrial Property (France); Search Report in Fench Pub. No. FR3016793, App. No. FR1450749; Sep. 11, 2014; National Institute of Industrial Property (France); France; all pages.
U.S. Patent & Trademark Office; Office Action in U.S. Appl. No. 13/158,761; Oct. 22, 2014; USPTO; Alexandria, Virgina; All Pages.
World Intellectual Property Organization; International Search Report and Written Opinion of the International Searching Authority for International App. No. WO2015114122, PCT Pub'n. No. PCT/EP2015/052019; May 13, 2015; WIPO; Geneva, Switzerland; all pages.
U.S. Patent & Trademark Office; Office Action in U.S. Appl. No. 14/594,770; Jul. 1, 2015; USPTO; Alexandria, Virgina; All Pages.
U.S. Patent & Trademark Office; Office Action in U.S. Appl. No. 14/594,770; Jan. 27, 2016; USPTO; Alexandria, Virgina; All Pages.
U.S. Patent & Trademark Office; Office Action in U.S. Appl. No. 10/276,712; Dec. 23, 2004; USPTO; Alexandria, Virgina; All Pages.
U.S. Patent & Trademark Office; Examiner's Interview Summary in U.S. Appl. No. 11/378,165; Nov. 26, 2012; USPTO; Alexandria, Virgina; All Pages.
U.S. Patent & Trademark Office; Office Action in U.S. Appl. No. 11/767,386; Apr. 24, 2013; USPTO; Alexandria, Virgina; All Pages.
U.S. Patent & Trademark Office; Office Action in U.S. Appl. No. 13/854,808; Apr. 18, 2014; USPTO; Alexandria, Virgina; All Pages.
U.S. Patent & Trademark Office; Office Action in U.S. Appl. No. 13/854,808; Jul. 7, 2014; USPTO; Alexandria, Virgina; All Pages.
U.S. Patent & Trademark Office; Office Action in U.S. Appl. No. 13/854,808; Jan. 23, 2015; USPTO; Alexandria, Virgina; All Pages.
U.S. Patent & Trademark Office; Office Action in U.S. Appl. No. 14/149,357; Jun. 30, 2015; USPTO; Alexandria, Virgina; All Pages.
U.S. Patent & Trademark Office; Office Action in U.S. Appl. No. 14/149,357; Sep. 11, 2015; USPTO; Alexandria, Virgina; All Pages.
U.S. Patent & Trademark Office; Office Action in U.S. Appl. No. 13/854,808; Nov. 27, 2015; USPTO; Alexandria, Virginia; All Pages
U.S. Patent & Trademark Office; Office Action in U.S. Appl. No. 14/149,357; Feb. 10, 2016; USPTO; Alexandria, Virginia; All Pages.
U.S. Patent & Trademark Office; Office Action in U.S. Appl. No. 13/854,808; Mar. 22, 2016; USPTO; Alexandria, Virginia; All Pages.
U.S. Patent & Trademark Office; Examiner Interview Summary in U.S. Appl. No. 13/854,808; Mar. 30, 2016, USPTO; Alexandria, Virginia; All Pages.
LDR Medical, by its attorneys; Chapter II amendments for PCT Pub'n No. WO2006120505, App. No. PCT/IB2005/004093; Oct. 30, 2006; WIPO; Geneva, Switzerland; All Pages.
LDR Medical, by its attorneys; Written Argument and Written Amendment for Pub'n No. JP2009532075, Application No. JP20080554874; May 15, 2012; Japan Patent Office; Tokyo, Japan; all pages.
U.S. Patent & Trademark Office; Notice of Allowance in U.S. Appl. No. 12/360,050; Aug. 2, 2012; USPTO; Alexandria, Virgina; All Pages.
LDR Medical, by its attorneys; Reply to Office Action in U.S. Appl. No. 12/884,664; Oct. 16, 2012; USPTO; Alexandria, Virginia; All Pages.
LDR Medical, by its attorneys; Reply to Office Action in U.S. Appl. No. 11/378,165; Nov. 5, 2012; USPTO; Alexandria, Virgina; All Pages.
LDR Medical, by its attorneys; Reply to Office Action in U.S. Appl. No. 13/158,761; Nov. 19, 2012; USPTO; Alexandria, Virgina; All Pages.
U.S. Patent & Trademark Office; Notice of Allowance in U.S. Appl. No. 11/378,165; Nov. 26, 2012; USPTO; Alexandria, Virgina; All Pages.
LDR Medical, by its attorneys; Reply to Office Action in U.S. Appl. No. 12/955,898; Dec. 3, 2012; USPTO; Alexandria, Virgina; All Pages.
LDR Medical, by its attorneys; Response to Statement of Reasons for Allowance in U.S. Appl. No. 11/378,165; Feb. 26, 2013; USPTO; Alexandria, Virginia; All Pages.
LDR Medical, by its attorneys; Reply to Office Action in U.S. Appl. No. 12/884,664; Apr. 10, 2013; USPTO; Alexandria, Virginia; All Pages.
LDR Medical, by its attorneys; Amendment for Pub'n No. EP2519194, Application No. EP20090812464; May 23, 2013; EPO; Munich, Germany; all pages.
LDR Medical, by its attorneys; Reply to Office Action in U.S. Appl. No. 12/955,898; Jul. 10, 2013; USPTO; Alexandria, Virginia; All Pages.

(56) References Cited

OTHER PUBLICATIONS

LDR Medical, by its attorneys; Reply to Office Action in U.S. Appl. No. 11/767,386; Jul. 24, 2013; USPTO; Alexandria, Virginia; All Pages.

LDR Medical, by its attorneys; Reply to Office Action in U.S. Appl. No. 13/158,761; Jul. 29, 2013; USPTO; Alexandria, Virginia; All Pages.

U.S. Patent & Trademark Office; Notice of Allowance in U.S. Appl. No. 12/884,664; Aug. 6, 2013; USPTO; Alexandria, Virgina; All Pages.

U.S. Patent & Trademark Office; Notice of Allowance in U.S. Appl. No. 11/767,386; Aug. 30, 2013; USPTO; Alexandria, Virgina; All Pages.

LDR Medical, by its attorneys; Reply to Office Action in U.S. Appl. No. 13/603,043; Oct. 9, 2013; USPTO; Alexandria, Virgina; All Pages.

LDR Medical, by its attorneys; Request for Continued Examination in U.S. Appl. No. 13/158,761; Nov. 14, 2013; USPTO; Alexandria, Virgina; All Pages.

LDR Medical, by its attorneys; Response to Statement of Reasons for Allowance in U.S. Appl. No. 11/767,386; Dec. 2, 2013; USPTO; Alexandria, Virgina; All Pages.

LDR Medical, by its attorneys; Response to International Search Report for International App. No. PCT/EP2013/053622, PCT Pub'n. No. WO 2013/124453; Dec. 18, 2013; WIPO; Geneva, Switzerland; all pages.

U.S. Patent & Trademark Office; Reply to Office Action in U.S. Appl. No. 13/616,448; Dec. 23, 2013; USPTO; Alexandria, Virginia; All Pages.

U.S. Patent & Trademark Office; Notice of Allowance in U.S. Appl. No. 13/616,448; Feb. 7, 2014; USPTO; Alexandria, Virginia; All Pages.

LDR Medical, by its attorneys; Reply to Office Action in U.S. Appl. No. 14/064,434; Apr. 14, 2014; USPTO; Alexandria, Virginia; All Pages.

U.S. Patent & Trademark Office; Notice of Allowance in U.S. Appl. No. 13/616,448; Apr. 21, 2014; USPTO; Alexandria, Virginia; All Pages.

LDR Medical, by its attorneys; Reply to Office Action in U.S. Appl. No. 13/603,043; May 21, 2014; USPTO; Alexandria, Virginia; All Pages.

LDR Medical, by its attorneys; Reply to Office Action in U.S. Appl. No. 13/854,808; Jun. 18, 2014; USPTO; Alexandria, Virginia; All Pages.

U.S. Patent & Trademark Office; Notice of Allowance in U.S. Appl. No. 13/774,547; Jul. 3, 2014; USPTO; Alexandria, Virgina; All Pages.

LDR Medical, by its attorneys; Reply to Office Action in U.S. Appl. No. 12/955,898; Aug. 4, 2014; USPTO; Alexandria, Virginia; All Pages.

U.S. Patent & Trademark Office; Notice of Allowance in U.S. Appl. No. 12/955,898; Aug. 8, 2014; USPTO; Alexandria, Virginia; All Pages.

LDR Medical, by its attorneys; Reply to Office Action in U.S. Appl. No. 14/064,434; Aug. 27, 2014; USPTO; Alexandria, Virginia; All Pages.

U.S. Patent & Trademark Office; Notice of Allowance in U.S. Appl. No. 14/064,434; Sep. 8, 2014; USPTO; Alexandria, Virginia; All Pages.

LDR Medical, by its attorneys; Reply to Office Action in U.S. Appl. No. 13/520,041; Sep. 19, 2014; USPTO; Alexandria, Virginia; All Pages.

LDR Medical, by its attorneys; Reply to Office Action in U.S. Appl. No. 13/538,078; Oct. 14, 2014; USPTO; Alexandria, Virginia; All Pages.

U.S. Patent & Trademark Office; Notice of Allowance in U.S. Appl. No. 13/774,547; Oct. 16, 2014; USPTO; Alexandria, Virgina; All Pages.

U.S. Patent & Trademark Office; Notice of Allowance in U.S. Appl. No. 13/538,078; Oct. 20, 2014; USPTO; Alexandria, Virgina; All Pages.

LDR Medical, by its attorneys; Reply to Office Action in U.S. Appl. No. 13/603,043; Dec. 24, 2014; USPTO; Alexandria, Virgina; All Pages.

LDR Medical, by its attorneys; Reply to Office Action in U.S. Appl. No. 13/585,063; Jan. 6, 2015; USPTO; Alexandria, Virgina; All Pages.

LDR Medical, by its attorneys; Reply to Office Action in U.S. Appl. No. 13/854,808; Jan. 7, 2015; USPTO; Alexandria, Virgina; All Pages.

LDR Medical, by its attorneys; Reply to Office Action in U.S. Appl. No. 13/438,352; Jan. 14, 2015; USPTO; Alexandria, Virgina; All Pages.

LDR Medical, by its attorneys; Reply to Office Action in U.S. Appl. No. 13/732,244; Jan. 20, 2015; USPTO; Alexandria, Virgina; All Pages.

U.S. Patent & Trademark Office; Notice of Allowance in U.S. Appl. No. 12/955,898; Jan. 29, 2015; USPTO; Alexandria, Virgina; All Pages.

U.S. Patent & Trademark Office; Notice of Allowance in U.S. Appl. No. 13/774,547; Feb. 2, 2015; USPTO; Alexandria, Virgina; All Pages.

U.S. Patent & Trademark Office; Notice of Allowance in U.S. Appl. No. 13/603,043; Feb. 10, 2015; USPTO; Alexandria, Virgina; All Pages.

U.S. Patent & Trademark Office; Notice of Allowance in U.S. Appl. No. 13/438,352; Mar. 2, 2015; USPTO; Alexandria, Virgina; All Pages.

LDR Medical, by its attorneys; Reply to Office Action in U.S. Appl. No. 13/520,041; Mar. 6, 2015; USPTO; Alexandria, Virgina; All Pages.

LDR Medical, by its attorneys; Reply to Office Action in U.S. Appl. No. 14/306,785; Apr. 22, 2015; USPTO; Alexandria, Virgina; All Pages.

LDR Medical, by its attorneys; Reply to Office Action in U.S. Appl. No. 13/158,761; Apr. 22, 2015; USPTO; Alexandria, Virgina; All Pages.

U.S. Patent & Trademark Office; Notice of Allowance in U.S. Appl. No. 13/158,761; May 12, 2015; USPTO; Alexandria, Virgina; All Pages.

LDR Medical, by its attorneys; Reply to Office Action in U.S. Appl. No. 13/854,808; Jul. 23, 2015; USPTO; Alexandria, Virgina; All Pages.

LDR Medical, by its attorneys; Reply to Office Action in U.S. Appl. No. 13/520,041; Aug. 10, 2015; USPTO; Alexandria, Virgina; All Pages.

LDR Medical, by its attorneys; Reply to Office Action in U.S. Appl. No. 13/585,063; Aug. 11, 2015; USPTO; Alexandria, Virgina; All Pages.

LDR Medical, by its attorneys; Reply to Office Action in U.S. Appl. No. 13/732,244; Aug. 20, 2015; USPTO; Alexandria, Virgina; All Pages.

LDR Medical, by its attorneys; Reply to Office Action in U.S. Appl. No. 14/149,357; Aug. 31, 2015; USPTO; Alexandria, Virgina; All Pages.

U.S. Patent & Trademark Office; Notice of Allowance in U.S. Appl. No. 13/158,761; Sep. 2, 2015; USPTO; Alexandria, Virgina; All Pages.

LDR Medical, by its attorneys; Reply to Office Action in U.S. Appl. No. 14/659,587; Sep. 16, 2015; USPTO; Alexandria, Virgina; All Pages.

LDR Medical, by its attorneys; Reply to Office Action in U.S. Appl. No. 14/306,785; Sep. 22, 2015; USPTO; Alexandria, Virgina; All Pages.

U.S. Patent & Trademark Office; Notice of Allowance in U.S. Appl. No. 13/158,761; Sep. 25, 2015; USPTO; Alexandria, Virgina; All Pages.

U.S. Patent & Trademark Office; Notice of Allowance in U.S. Appl. No. 14/659,587; Oct. 9, 2015; USPTO; Alexandria, Virgina; All Pages.

(56) References Cited

OTHER PUBLICATIONS

U.S. Patent & Trademark Office; Notice of Allowance in U.S. Appl. No. 14/306,785; Oct. 13, 2015; USPTO; Alexandria, Virgina; All Pages.

LDR Medical, by its attorneys; Reply to Office Action in U.S. Appl. No. 14/594,770; Nov. 2, 2015; USPTO; Alexandria, Virgina; All Pages.

LDR Medical, by its attorneys; Notice of Allowance in U.S. Appl. No. 13/520,041; Nov. 18, 2015; USPTO; Alexandria, Virgina; All Pages.

LDR Medical, by its attorneys; Reply to Office Action in U.S. Appl. No. 14/149,357; Dec. 11, 2015; USPTO; Alexandria, Virgina; All Pages.

LDR Medical, by its attorneys; Reply to Office Action in U.S. Appl. No. 14/721,818; Dec. 28, 2015; USPTO; Alexandria, Virgina; All Pages.

LDR Medical, by its attorneys; Reply to Office Action in U.S. Appl. No. 13/732,244; Jan. 20, 2016; USPTO; Alexandria, Virgina; All Pages.

LDR Medical, by its attorneys; Reply to Office Action in U.S. Appl. No. 13/585,063; Feb. 4, 2016; USPTO; Alexandria, Virgina; All Pages.

LDR Medical, by its attorneys; Reply to Office Action in U.S. Appl. No. 13/854,808; Feb. 29, 2016; USPTO; Alexandria, Virgina; All Pages.

U.S. Patent & Trademark Office; Notice of Allowance in U.S. Appl. No. 13/520,041; Mar. 8, 2016; USPTO; Alexandria, Virgina; All Pages.

LDR Medical, by its attorneys; Reply to Office Action in U.S. Appl. No. 14/594,770; Apr. 27, 2016; USPTO; Alexandria, Virgina; All Pages.

LDR Medical, by its attorneys; Reply to Office Action in U.S. Appl. No. 14/659,587; Apr. 28, 2016; USPTO; Alexandria, Virginia; All Pages.

LDR Medical, by its attorneys; Reply to Office Action and Notice of Appeal in U.S. Appl. No. 14/721,818; May 2, 2016; USPTO; Alexandria, Virginia; All Pages.

LDR Medical, by its attorneys; Reply to Office Action in U.S. Appl. No. 13/585,063; May 4, 2016; USPTO; Alexandria, Virginia; All Pages.

\* cited by examiner

INTERSOMATIC CAGE, INTERVERTEBRAL PROSTHESIS, ANCHORING DEVICE AND IMPLANTATION INSTRUMENTS

RELATED APPLICATIONS

This application is a divisional of U.S. patent application Ser. No. 12/134,884 filed Jun. 6, 2008, and issuing as U.S. Pat. No. 8,343,219 on Jan. 1, 2013, which claims priority under 35 U.S.C. §119 to French Patent Application No. 07 04155, filed in FRANCE on Jun. 8, 2007.

TECHNICAL FIELD

This present invention concerns the area of orthopedic implants and more precisely of spinal implants, such as intervertebral prostheses and intersomatic cages.

BACKGROUND

An intervertebral prosthesis is implanted between two adjacent vertebrae in order to maintain or restore a space between the vertebrae while also preserving good mobility. An intersomatic cage is implanted between two adjacent vertebrae to allow the insertion and the growth of grafts of bony tissue (or a substitute) in the disc space, in order to achieve an arthrodesis (fusion of two vertebrae). After insertion of the cage, the intervertebral space may be filled with self-adapting spongy bone or suitable bony substitutes. The present invention concerns intervertebral prostheses and intersomatic cages for intervertebral fusion grafting and their attachment to the vertebrae by a bony anchoring device and their implantation in the disc space using implantation instruments.

A problem in this area concerns the stability of the intervertebral prostheses or of the intersomatic cages in the disc space after they have been implanted there, at least before the growth of the graft on either side of the cage and fusion with the vertebrae in the case of the intersomatic cages. For example, there exists a risk that the prosthesis or the cage will move within the intervertebral space under the effect of the stresses exerted upon it when the patient moves. The prosthesis or the cage must therefore not only have a shape that prevents it from pivoting but also have resources to prevent it from moving within the intervertebral space.

From previous designs, we know of solutions that consist of equipping the top and bottom surfaces of the prostheses or cages with notches so as to prevent movement. However, this type of solution is not perfect and the prosthesis or the cage still may move. We are also familiar, from previous designs, with solutions that consist of equipping the prosthesis or the cage with a bony anchoring device which is used to soundly attach the prosthesis or the cage to the vertebral plates of the vertebrae between which it is implanted. This type of bony anchoring device proves to be effective for securing the prosthesis or the cage. However, this type of solution presents problems during implantation.

Access to the intervertebral spaces is often particularly difficult because of the dimensions involved, and in particular due to the presence of blood vessels and nerves at the edges of the intervertebral space. The bony anchoring devices must penetrate into the vertebrae to a sufficient depth to secure the device. As a consequence, these bony anchoring devices are generally implanted along an approach axis that is more-or-less perpendicular to the plane of the intervertebral space or at least on a substantially oblique axis in relation to the plane of the intervertebral space. Other types of bony anchoring devices fit onto a plate that is substantially parallel to the axis of the vertebral column and extending the prosthesis or the cage on one of the faces of the vertebrae. These different types of device therefore require the surgeons to make large incisions, inducing prejudice and considerable risks for the patient. In addition, this type of bony anchoring device is not easy to implant since it requires that there is sufficient space at the edges of the intervertebral space to allow the implantation of the device, which unfortunately is not always the case, depending on the vertebrae in question.

In this context, it is useful to provide an anchoring device (which may be referenced below simply as a "device") for an intersomatic cage or an intervertebral disc prosthesis that reduces the space at the edges of the intervertebral space that is necessary for the implantation of the cage itself, that makes the application of the anchoring device more convenient, or that provides better anchoring than some of the known anchoring means.

SUMMARY

Some embodiments of this present invention have a purpose of overcoming certain drawbacks of some previous designs by providing an anchoring device that is implanted solidly and at a sufficient depth in the vertebral plates to retain the cage against these vertebrae, but on an approach axis that is substantially along the plane of the intervertebral space.

Some embodiments of this present invention have a purpose of overcoming certain drawbacks of some previous designs by providing an intersomatic cage that is implantable substantially along the plane of the intervertebral space, which may be attached to the vertebrae by means of an anchoring device that is implantable substantially along the plane of the intervertebral space.

Some embodiments of this present invention have a purpose of overcoming certain drawbacks of some previous designs by providing an intervertebral prosthesis that is implantable substantially along the plane of the intervertebral space, which may be solidly attached to the vertebrae by means of an anchoring device that is implantable substantially along the plane of the intervertebral space.

Some embodiments of this present invention have a purpose of overcoming certain drawbacks of some previous designs by providing an instrument for the implantation of an intersomatic cage or an intervertebral disc prosthesis between the vertebrae and for the implantation of an anchoring device in at least one of these vertebrae, which may be used to implant the cages or the prostheses substantially along the plane of the intervertebral space and to implant an anchoring device on an approach axis that is substantially along the plane of the intervertebral space.

BRIEF DESCRIPTIONS OF THE DRAWINGS

Figure 1B:
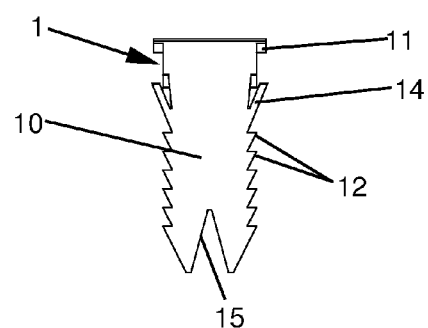
Figure 1C:
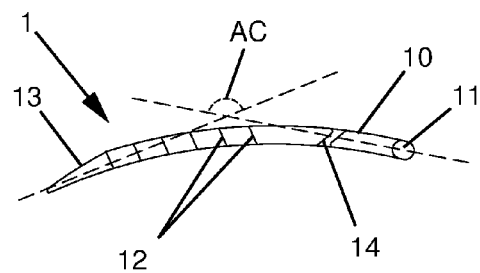
Figure 1D:
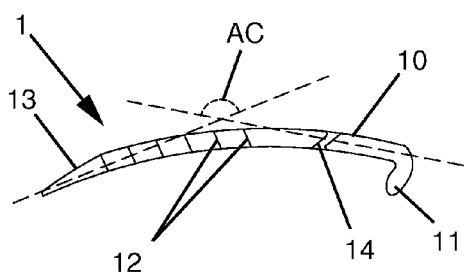

Other particular features and advantages of various embodiments of this present invention will appear more clearly on reading the description that follows, provided with reference to the appended drawings, in which:

FIG. 1A represents a view in perspective of an anchoring device according to one method of implementation of the invention, FIG. 1B represents a view from above of an anchoring device according to another method of implementation of the invention, and FIGS. 1C and 1D represent views in profile of anchoring devices according to two different methods of implementation of the invention.

Figure 2A:
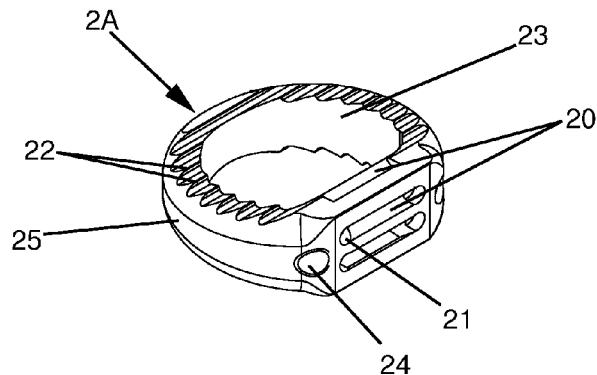
Figure 2B:
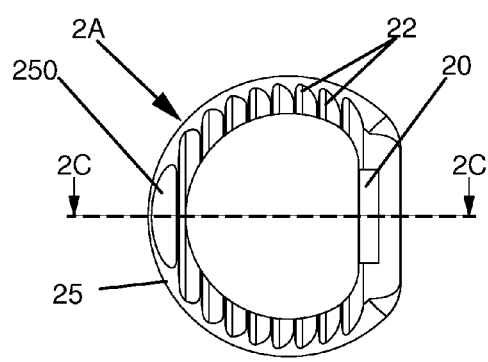
Figure 2C:
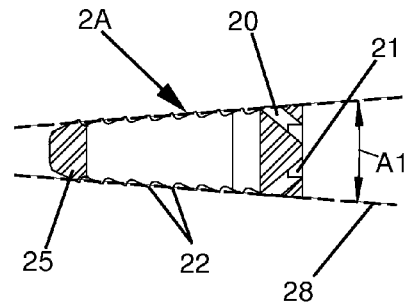
Figure 2D:
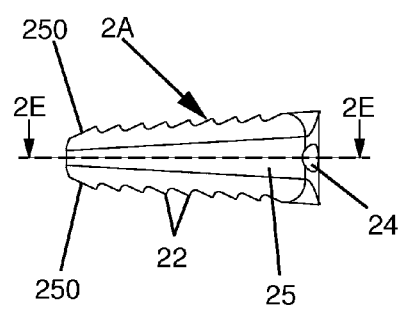
Figure 2E:
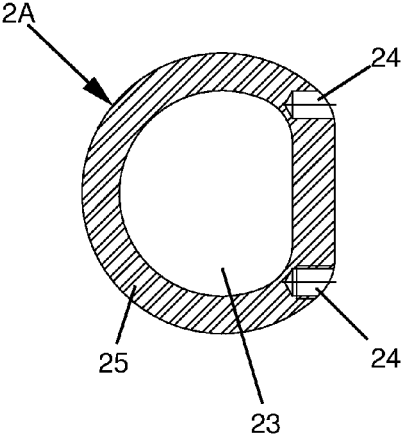

FIGS. 2A, 2B and 2D respectively represent a view in perspective, a view from above and a view in profile of an intersomatic cage according to one method of implementation of the invention, FIG. 2C represents a view in section of this intersomatic cage on section plane 2C-2C represented in FIG. 2B and FIG. 2E represents a view in section of this intersomatic cage on section plane 2E-2E represented in FIG. 2D.

Figure 3A:
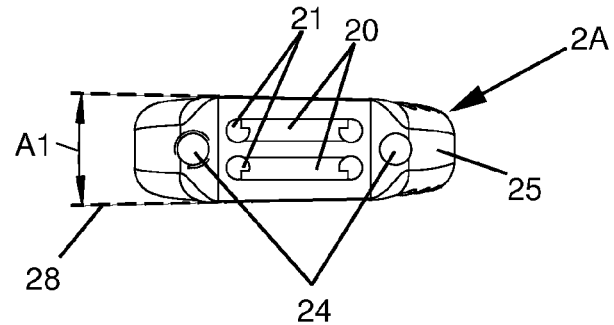
Figure 3B:
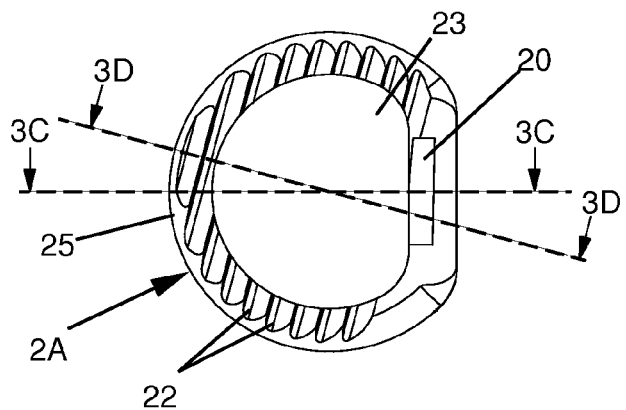
Figure 3C:
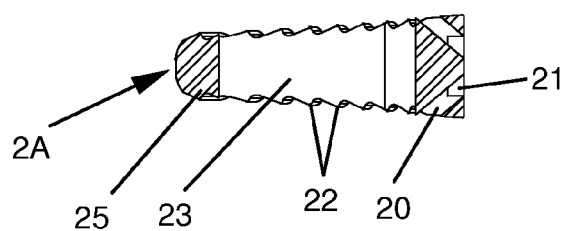
Figure 3D:
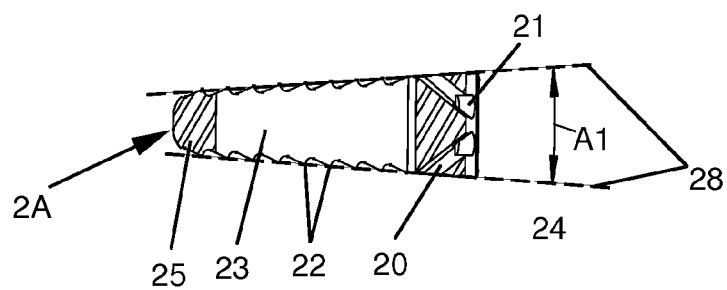

FIGS. 3A and 3B respectively represent a view in perspective from the front and a view from above of an intersomatic cage according to one method of implementation of the invention, FIG. 3C represents a view in section of this intersomatic cage on section plane 3C-3C represented in FIG. 3B and FIG. 3D represents a view in section of this intersomatic cage on section plane 3D-3D represented in FIG. 3B.

Figure 4A:
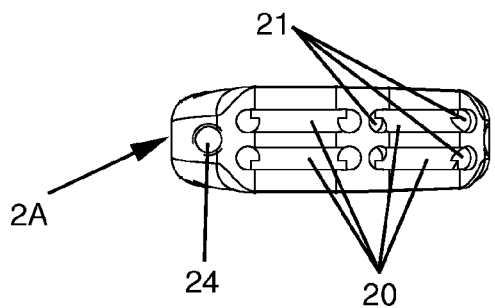
Figure 4B:
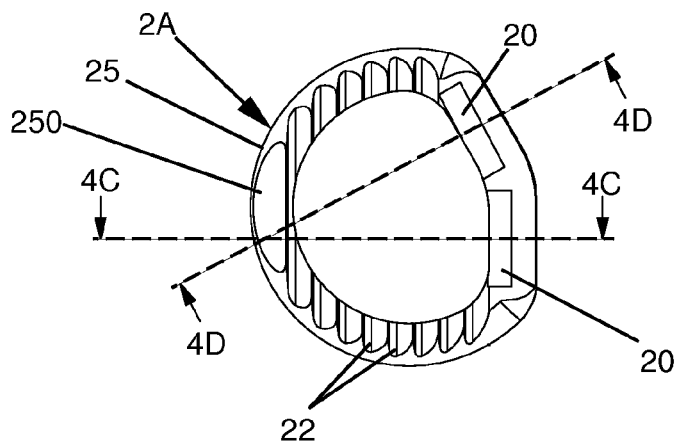
Figure 4C:
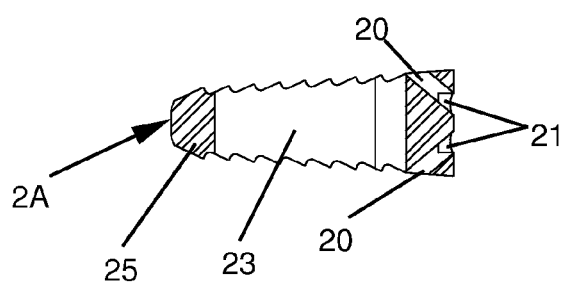
Figure 4D:
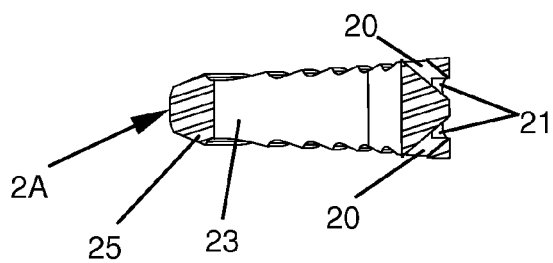

FIGS. 4A and 4B respectively represent a view in perspective from the front and a view from above of an intersomatic cage according to one method of implementation of the invention, FIG. 4C represents a view in section of this intersomatic cage on section plane 4C-4C represented in FIG. 4B, and FIG. 4D represents a view in section of this intersomatic cage on section plane 4D-4D represented in FIG. 4B.

Figure 5A:
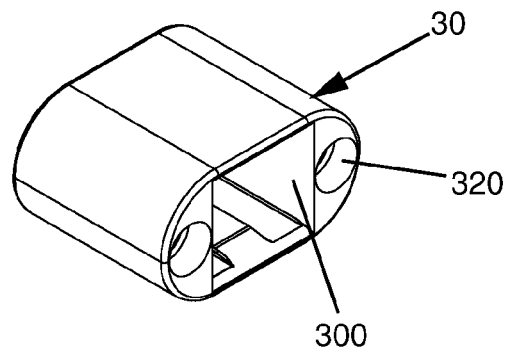
Figure 5B:
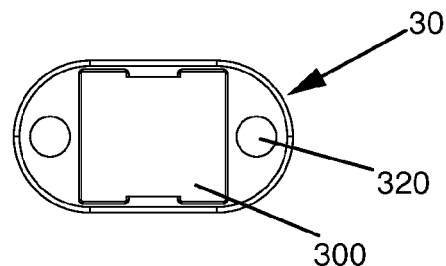
Figure 5C:
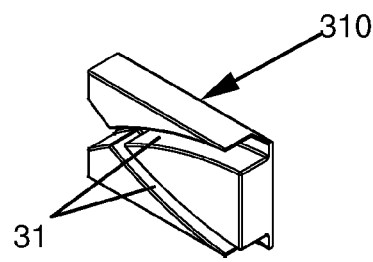
Figure 5D:
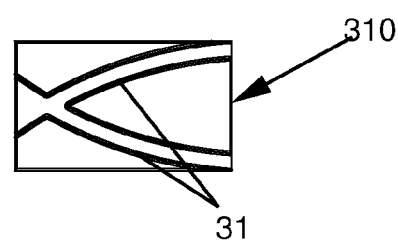
Figure 5E:
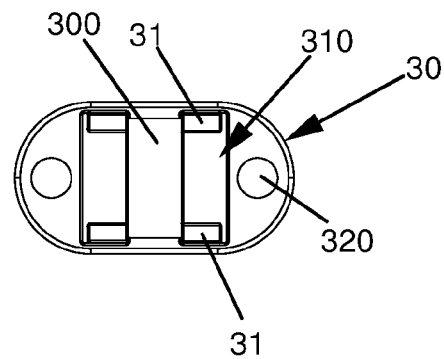

FIGS. 5A and 5B respectively represent a view in perspective and a view from the front of a head for the implantation guide of an anchoring device according to one method of implementation of the invention, FIGS. 5C and 5D respectively represent a view in perspective and a view in profile of a guidance element for an anchoring device according to one method of implementation of the invention and FIG. 5E represents a view from the front of the head of the guide equipped with two guidance elements according to one method of implementation of the invention.

Figure 6A:
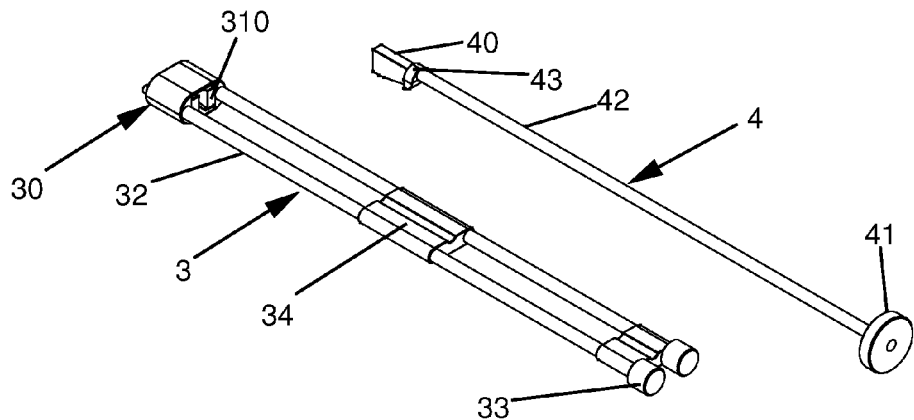
Figure 6B:
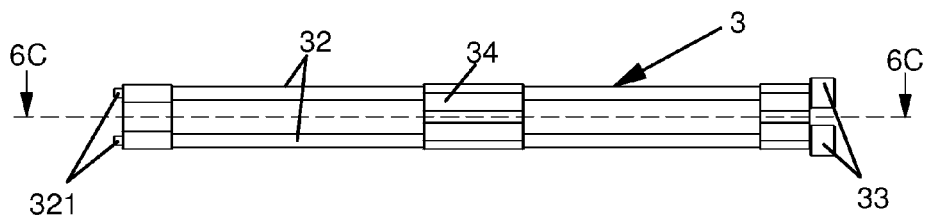
Figure 6C:
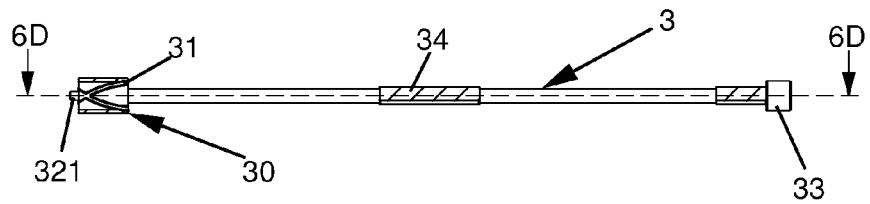
Figure 6D:
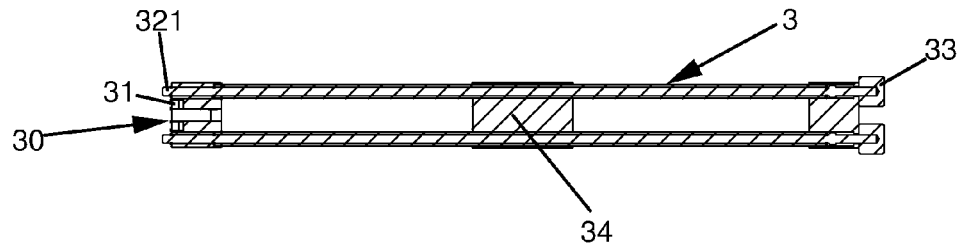
Figure 6E:
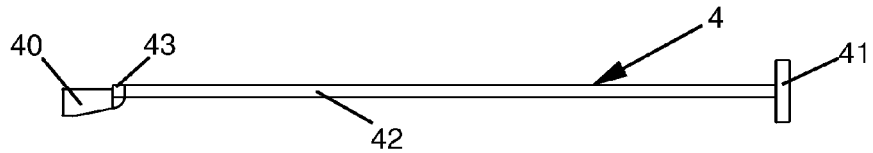

FIG. 6A represents a view in perspective of an implantation guide and of an impactor according to one method of implementation of the invention, FIGS. 6B, 6C and 6D respectively represent a view from above, a view in section on section plane 6C-6C represented in FIG. 6B and a view in section on section plane 6D-6D represented in FIG. 6C of an implantation guide according to one method of implementation of the invention and FIG. 6E represents a view in profile of an impactor according to one method of implementation of the invention.

Figure 7A:
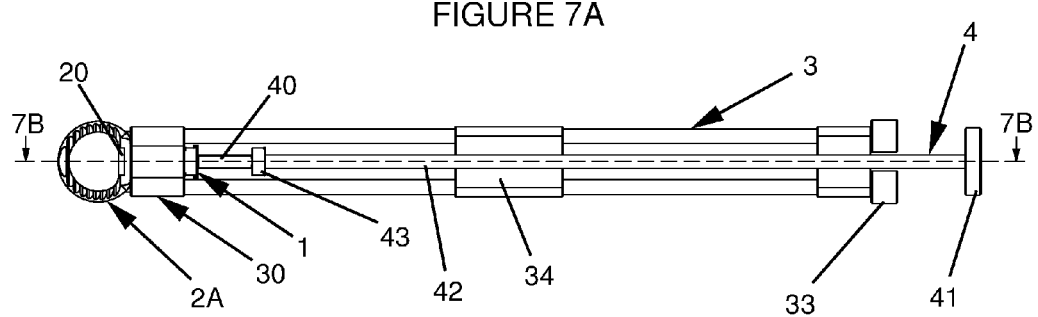
Figure 7B:
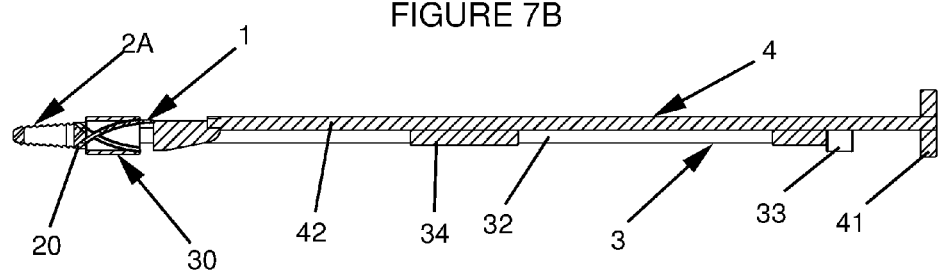
Figure 7C:
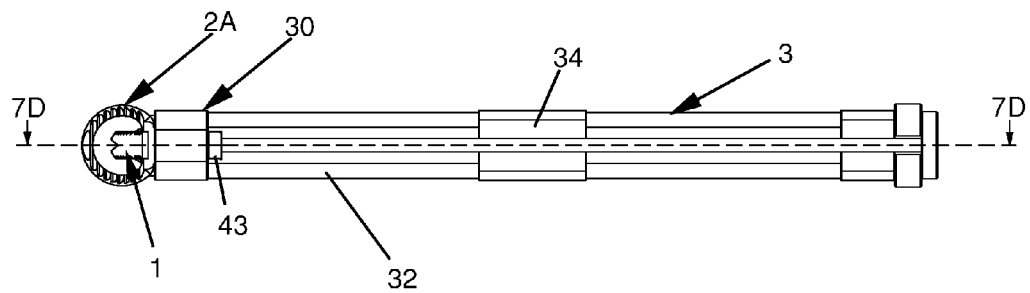
Figure 7D:
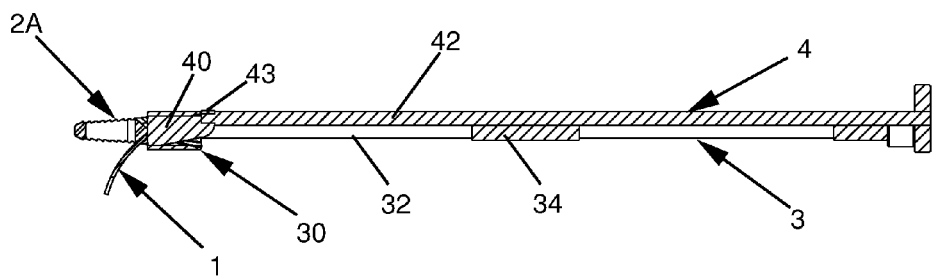

FIGS. 7A and 7C represent views from above of an assembly according to one method of implementation of the invention, of an implantation guide, of an impactor, of a cage and of an anchoring device, respectively, ready to be impacted and impacted, FIGS. 7B and 7D represent views in section of this assembly along section plane 7B-7B represented in FIG. 7A and section plane 7D-7D represented in FIG. 7C, respectively.

Figure 8A:
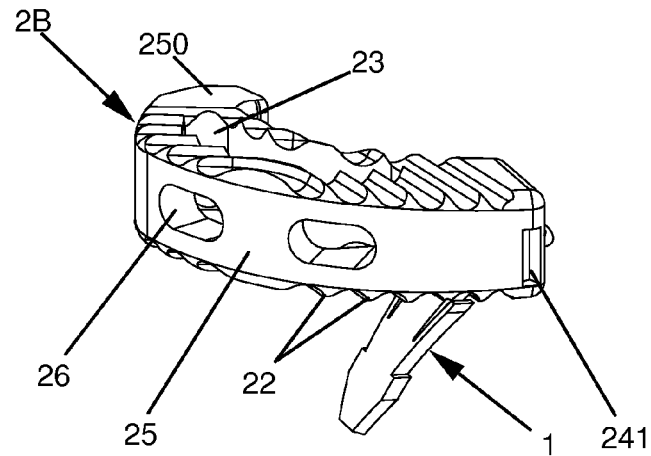
Figure 8B:
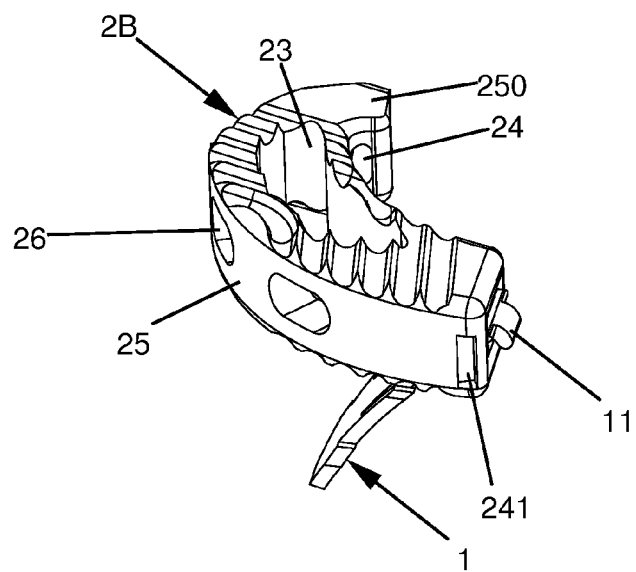
Figure 8C:
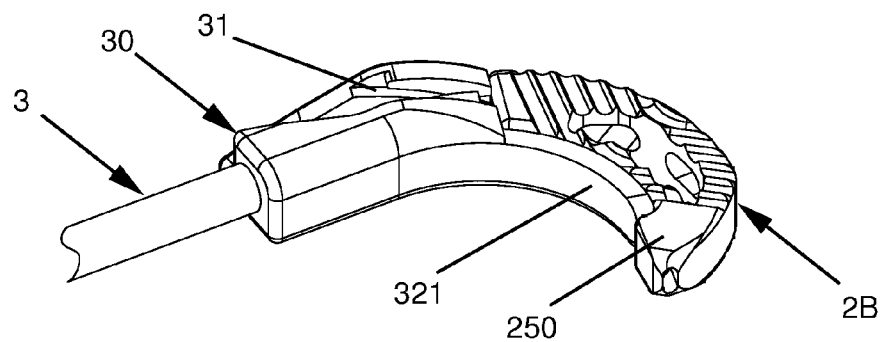

FIGS. 8A and 8B represent views in perspective of an intersomatic cage equipped with an anchoring device according to one method of implementation of the invention and FIG. 8C represents a view in perspective of the end of an implantation guide carrying an intersomatic cage according to one method of implementation of the invention.

Figure 9A:
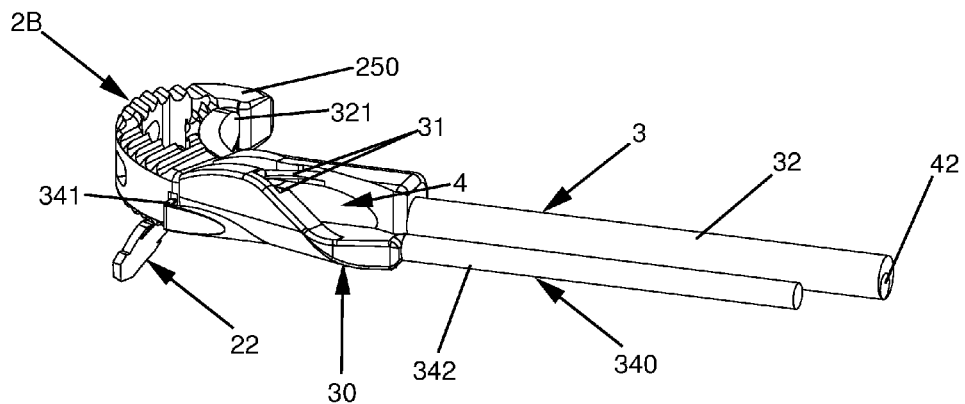
Figure 9B:
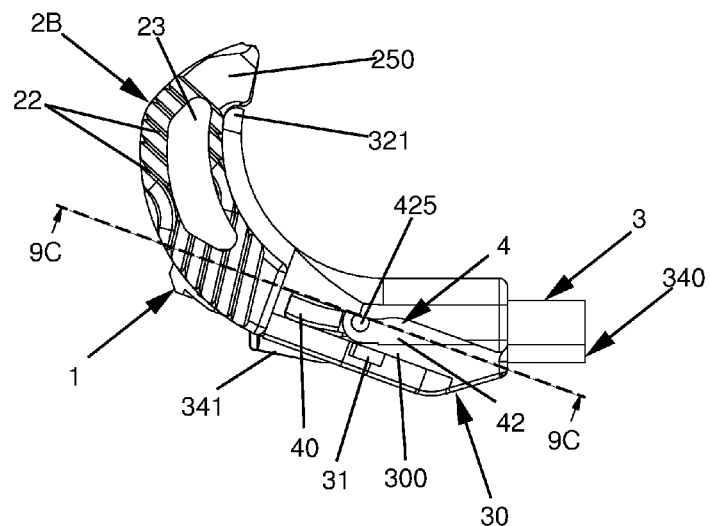
Figure 9C:
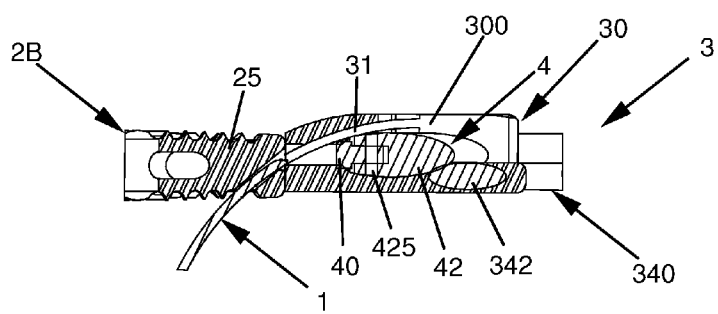

FIGS. 9A and 9B respectively represent a view in perspective and a view from above, of the end of an implantation guide carrying an intersomatic cage equipped with an anchoring device according to one method of implementation of the invention and FIG. 9C represents a view in section on section plane 9C-9C represented in FIG. 9B.

Figure 10A:
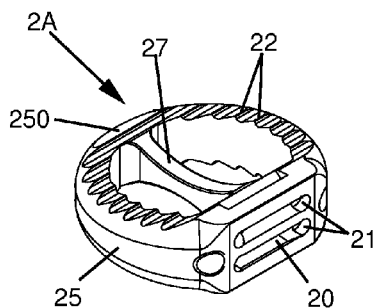
Figure 10D:
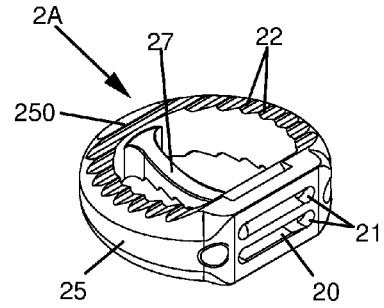
Figure 10B:
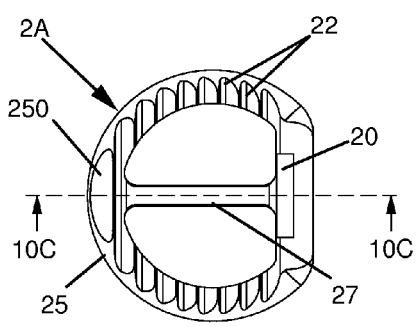
Figure 10E:
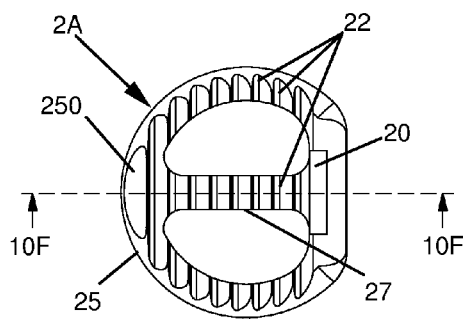
Figure 10C:
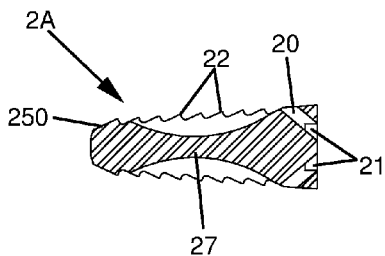
Figure 10F:
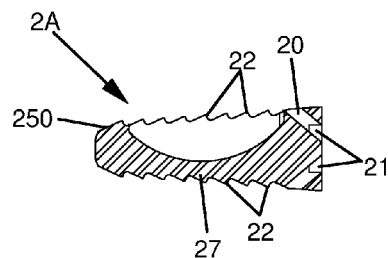

FIGS. 10A, 10B and 10C respectively represent a view in perspective, a view from above and a view in section along axis 10C-10C of FIG. 10B, of one method of implementation of a braced intersomatic cage and FIGS. 10D, 10E and 10F respectively represent a view in perspective, a view from below and a view in section along axis 10E-10F of FIG. 10E, of another method of implementation of a braced intersomatic cage.

Figure 11A:
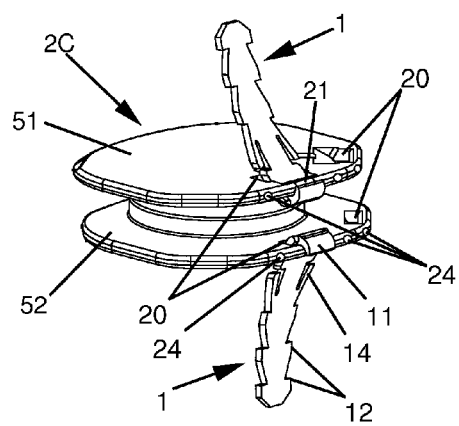
Figure 11C:
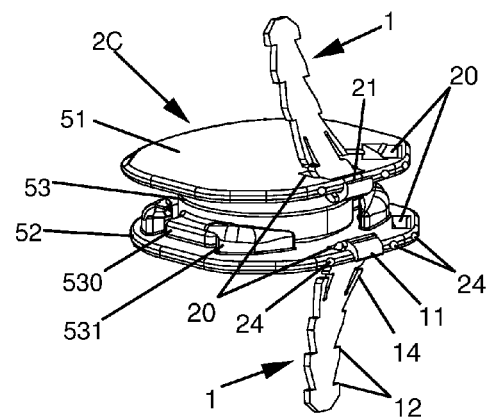
Figure 11B:
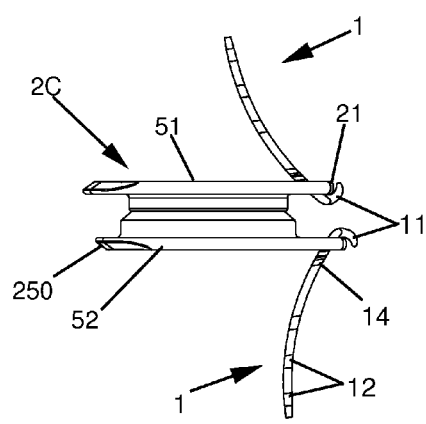
Figure 11D:
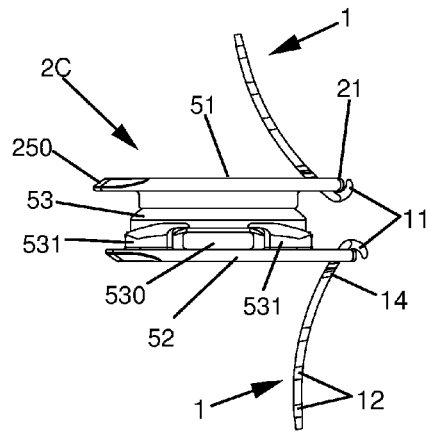

FIGS. 11A and 11B respectively represent a view in perspective and a view in profile of one method of implementation of an intervertebral prosthesis equipped with anchoring devices, and FIGS. 11C and 11D respectively represent a view in perspective and a view in profile of another method of implementation of an intervertebral prosthesis equipped with anchoring devices.

DETAILED DESCRIPTION OF VARIOUS EMBODIMENTS

This present invention concerns an anchoring device (1) that is usable for intersomatic cages (2A, 2B) or intervertebral disc prostheses (2C). In various embodiments, the anchoring device (1) fits onto at least one slot (20) located on the cage (2A, 2B) or the prosthesis (2C) that it secures. This present invention also concerns intersomatic cages (2A, 2B) and intervertebral disc prostheses (2C), which in various embodiments may have a slot (20) or other receptacles adapted to receive the anchoring device (1). This present invention also concerns an instrument for the implantation of a cage (2A, 2B) or of a prosthesis (2C) and for implantation of an anchoring device to secure the cage (2A, 2B) or the prosthesis (2C). In various embodiments, the instrument is designed for the anchoring device (1) so as to secure the latter in the vertebrae and also to the intersomatic cages (2A, 2B) or to the intervertebral disc prostheses (2C), which include at least one means (24) of retaining or attaching an implantation instrument so as to allow them to be gripped or otherwise engaged by the instrument. This attachment device may include at least one recess (24) that accommodates at least one gripping resource (321) of the instrument, as shown in the Figures and described below in greater detail. However, this attachment resource (24) may also include a portion projecting on the outside of the cage or of the prosthesis and that is inserted into a recess of a gripping resource (not shown). In addition, in certain implementation variants, this attachment resource (24) may be formed at least in part by different surfaces of the cage (2A, 2B) or of the prosthesis (2C), with the gripping resources (321) of the instrument then having a shape that is complementary to these surfaces so as to allow gripping of the cage or of the prosthesis.

Various embodiments allow a reduction in the dimensions of the device and of the associated instrument, so as to allow implantation of the anchoring device on an approach axis that is substantially along the plane of the intervertebral space (disc space).

The anchoring device (1) also may include a body (10) of elongated shape along a longitudinal axis extending between a first end and a second end. In this present description, the first end is called the penetration end and the second end is called the abutment end. The body (10) of the anchoring device (1) of various embodiments may have a curved shape that, along the longitudinal axis, describes an arc, for example a circular arc or an elliptic arc, whose dimensions and radius (or radii) of curvature are designed in such a manner that the anchoring device (1) is implantable in the vertebral plate of a vertebra by presenting the longitudinal axis of the device (1) approximately along the plane of the intervertebral space. Various implementation variants may feature a differing radius (or radii) of curvature of the anchoring device (1). The device also may have several different radii of curvature on different portions of the body (10), or may have a radius of curvature that varies along the body (10). Thus, this body may, for example, have a shape of a circular arc or of an elliptic arc, but may also describe a more complex curvature, such as if several circular arcs, having the same radius of curvature or different radii of curvature, were end to end or if several elliptic arcs, having the same radius of curvature or different radii of curvature, were end to end, or even any combination thereof, or even a radius of curvature that is a function of position along the body. In the present description, the terms "arc," "circular arc," and "radius of curvature" correspond to all these possibilities.

Accordingly, some embodiments of this present invention provide different implementation variants regarding the radius of curvature of the anchoring device (1). For example, depending on the use of the device (1), and in particular of the vertebrae between which the cage or the prosthesis is to be implanted, the device (1) preferably may have a radius of curvature that is greater or smaller in dimension in various places. Depending on the radius of curvature of the anchoring device (1), the axes passing respectively through the penetration end and through the abutment end of the device (1) form an angle (AC), as may be seen particularly in FIGS. 1C and 1D. This angle (AC) typically will be in the range of 90° to 180°, inclusively, although it may also be chosen to be less than 90°. Preferably, the angle (AC) will be between 110° and 160°, which in many circumstances will facilitate the implantation of the device better than an angle (AC) outside this range. Depending on the securing arrangement desired, an angle (AC) may be chosen that is substantially open. For example, if it is desired to secure the cage or the prosthesis by flattening it solidly against the vertebral plates, an angle (AC) will be chosen that ranges from 120° to 180°, while if instead it is desired to secure the cage or the prosthesis so as to prevent its movement in the plane of the disc space, an angle (AC) will be chosen that is between 90° and 150°. Different implementation variants may provide different angles for the anchoring device (1) to secure the cage or the prosthesis. In one of the preferred methods of implementation, angle (AC) may have a mutually accommodating value, such as close to 135°, for example, for securing the device by both flattening the cage or the prosthesis against a vertebral plate and inhibiting the movement of the cage or the prosthesis in the plane of the disc space.

In addition, depending on the method of implementation of the cage or of the prosthesis, it is possible to choose different angles for the device, in particular to promote secure fixing despite a natural or pathological lordosis or one imposed by the prosthesis. The anchoring device (1) may be inserted through a slot (20) located on at least one peripheral wall of the cage (2A, 2B) or on at least one plate of the intervertebral disc prosthesis (2C) and traverse at least one portion of this cage (2A, 2B) or of this prosthesis (2C). This slot (20) may extend from a peripheral surface of the wall (25) of the cage (2A, 2B) or of the plate of the prosthesis (2C) up to a top or bottom surface of this cage (2A, 2B) or of this plate, with an orientation designed for the radius of curvature of the anchoring device (1), so as to orientate the latter in the direction of the vertebral plate of one of the vertebrae between which the cage (2A, 2B) or the prosthesis is implanted. By means of this orientation of the slot (20), the anchoring device (1) may penetrate into at least one vertebral plate and secure the cage (2A, 2B) or the prosthesis (2C) against this vertebral plate. Depending on the radius of curvature and the angle (AC) of the anchoring device (1), the thickness and the orientation of the slot (20) may vary in accordance with the various methods of implementation.

Some embodiments of this present invention therefore provide an intersomatic cage (2A, 2B) that includes a peripheral wall (25) forming a cavity (23) that receives a graft of bony tissue or a substitute. Such a cage may include a cavity (23) in its centre, formed by its wall (25), as shown in the Figures, but it may also, in other implementation variants, consist of a block that does not have a cavity inside it, such cage being, for example, used at least in pairs, so as to form a cavity between the cages as is known from the previous designs. In an implementation variant represented in FIG. 10A, the intersomatic cage (2A) includes a brace (27) traversing its cavity (23) from side to side, which may be configured to strengthen the wall (25) of the cage (2A). This brace (27) may have different forms and orientations and may, for example, be orientated along the insertion axis of the cage (2A) between the vertebrae. In various methods of implementation, the brace (27) may have a height that is less than that of the rest of the cage. This smaller height of the brace (27) in relation to the rest of the cage may allow the cage to hug any shape irregularities of the vertebral plates. Thus, as illustrated, for example, in FIGS. 10A to 10C, the top and bottom surfaces of the brace (27) are located lower and higher than the top and bottom surfaces, respectively, of the cage (2A). Thus, if the vertebral plates of the two adjacent vertebrae have bumps, the cage will follow the shape of these plates and generally provide better stability. In this implementation example represented in FIGS. 10A to 10C, the brace is not equipped with notches since it will not be in contact with the vertebral plates. However, the brace (27) may nevertheless be equipped with notches (22), even in this case, for example, so as to enhance stability of the cage when the osseous graft has grown around the cage. In the implementation example of FIGS. 10D to 10F, the bottom surface of the brace (27) is located at the same level as the bottom surface of the rest of the cage (2A) but the top surface of the brace (27) is located lower than the top surface of the rest of the cage (2A), as may be seen particularly in FIG. 10E. In this implementation example, the bottom surface of the brace (27) is equipped with notches (22) adding to the notches present on the rest of the cage in order to oppose the movement of the latter. In a variant, this brace may not include notches. In a variant, this type of cage may also be used in an inverse configuration in relation to this example. Thus, in this variant, the brace (27) will have a top surface at the same level as the top surface of the rest of the cage and a bottom surface located higher than the rest of the cage. All of these possible variants of the brace may naturally be combined with the other variants concerning the other characteristics of the cage.

In some embodiments of this present invention, the wall (25) of the cage (2A, 2B) includes at least one slot (20) having a width that allows the passage of this anchoring device (1) despite its curvature. This slot (20) may have a width (the height of the aperture described by the slot) substantially larger than the height of the anchoring device (1), to increase the ease of such passage. This slot (20) traverses the cage (2A, 2B) between a peripheral surface of the wall (25) and a top or bottom surface of the cage (2A, 2B), with an orientation that is designed for the radius of curvature of the anchoring device (1), so as to orientate the latter in the direction of the vertebral plate of one of the vertebrae between which the cage (2A, 2B) is implanted.

Some embodiments of this present invention provide an intervertebral disc prosthesis (2C). The prosthesis (2C)

includes at least one first plate (51) and one second plate (52) that articulate along a curved surface. In one method of implementation, particularly visible in FIGS. 11A and 11B, the prosthesis (2C) includes only two plates (51, 52), each of which has a curved surface. These curved surfaces of the two plates (51, 52) are complementary and fit together to allow an articulation of plates (51, 52) by rotation about an axis that is more-or-less perpendicular to the plane of the plates and/or by sloping the plates in relation to each other. In another method of implementation that is particularly visible in FIGS. 11C and 11D, the prosthesis (2C) includes two plates (51, 52) and a central core (53), which is mobile in relation to at least one of the plates (51, 52). In one method of implementation, this core (53) includes a surface that is substantially plane, fitting onto a surface that is substantially plane of one of the plates (51, 52) and a curved surface fitting onto a complementary curved surface of the other plate (52, 51). The curved surface allows an articulation as described previously (inclination and/or rotation) and the plane surface allows a linear movement of the core in relation to the plate that includes the plane surface and/or a rotation of the core in relation to this plate, about an axis that is more-or-less perpendicular to the plane of the plates. In addition, according to the methods of implementation employed, the core (53) may include complementary mating resources (530) on at least one of the plates (51, 52) so as to limit the movement of the core (53) in rotation and/or in linear movement in relation to this plate. In some embodiments of the present invention, at least one of the plates (51, 52) of the prosthesis (2C) includes at least one slot (20) having a width that that allows the passage of this anchoring device (1) despite its curvature. This slot (20) may have a width (the height of the aperture described by the slot) substantially larger than the height of the anchoring device (1). Similar to some embodiments having an intersomatic cage (2A, 2B) discussed above, the intervertebral prosthesis (2C) may have one or more slots (20) that traverse the plate (51, 52) and orient the anchoring device (1) in the direction of the vertebral plate of one of the vertebrae between which the prosthesis (2C) is implanted. In some embodiments, the dimensions and orientation of the slot(s) (20) may be adapted, respectively, to the dimensions and to the radius of curvature of the anchoring device (1).

In a preferred method of implementation of the invention, the width of the slot (20) will be slightly greater than the thickness of the anchoring device (1), sufficiently to allow the passage of the latter within the slot, but by sufficiently little to enhance retention of the cage (2A, 2B) or of the prosthesis (2C) by the anchoring device (1), without excessive play of the latter within the slot (20). In various embodiments, the curvature of the device (1) along the abutment end may be configured to interfere with the slot (20) sufficiently to enhance the retention of the cage (2A, 2B) or of the prosthesis (2C) by the anchoring device (1). In certain methods of implementation of the invention, the length of the slot (20) may be substantially to the same as the width of the device (1) so that the latter has little or no play once inserted into the slot (20). The length of the anchoring device (1) may be designed for the depth of the slot (20) to be traversed and to the depth to which it must penetrate to the vertebral plates.

Thus, the anchoring device (1), by means of its radius of curvature and the orientation of the slot (20) in which it is inserted, may be implanted on an approach axis that is substantially along the plane of the intervertebral space, meaning the plane along which the cage (2A, 2B) or the prosthesis (2C) is implanted, which facilitates the approach of all of the elements of the intervertebral prosthesis or cage and the anchoring device to the edges of the intervertebral space. In one method of implementation, the arc described by the body (10) has dimensions and a radius of curvature that are designed in such a manner that the anchoring device (1) is implantable in a vertebral plate on an approach axis forming an angle with the vertical axis of the vertebral column of between 40° and 140°, and preferably an angle of approximately 90°. This angle may vary for a given anchoring device (1) depending on the dimensions at the edges of the vertebrae, and may also vary from one anchoring device (1) to another depending on the radius of curvature of the device (1) used and the angle (AC) formed between its abutment and penetration ends.

In one method of implementation of the invention, the curved and elongated body (10) includes at least one curved plate, as may be seen particularly in FIG. 1 (A to D). This plate may be substantially rectangular as shown in the Figures, but may naturally have various shapes without moving outside the spirit of the invention. Likewise, in other implementation variants, the body (10) may include a curved rod, with the slot (20) then having a shape to suit the section of this rod, but the invention naturally allows other methods of implementation, in particular regarding the shape of the body (10). In other implementation variants (not shown), the body (10) of this anchoring device (1) may include two plates (or two rods), generally parallel to each other, and connected together at the abutment end by an inward-curving part that fits onto a rod present at the centre of the slot (20) in the cage, for example as described in U.S. patent application Ser. No. 10/483,563, or U.S. patent application Ser. No. 11/109,276, each of which is incorporated herein by reference.

The penetration end of the anchoring device (1) penetrates into the vertebral plate of one of the vertebrae between which the cage (or the prosthesis) is to be implanted. In one method of implementation of the invention, the penetration end includes a chamfer (13) or a bevel to facilitate the penetration of the device (1) into the vertebra, as may be seen particularly in FIGS. 1C and 1D. In an implementation variant, this penetration end may also include an indentation (15), in the form of a V-shaped notch, for example, as shown in FIG. 1B, to facilitate the penetration of the penetration end into the vertebral plates. The abutment end is butted up against a surface of the cage or of the prosthesis that the device secures, so as to hold the latter against the vertebral plate, preferably firmly and tightly.

In different implementation variants of the anchoring device (1), the abutment end of the body (10) includes at least one stop element (11) that mates with at least one surface of the cage (2A, 2B) or of the prosthesis (2C) that the device (1) secures. In a complementary manner, in different implementation variants of the cage (2A, 2B) or of the prosthesis (2C), at the level of the peripheral surface of the wall (25), the slot (20) includes at least one stop element surface (21) that mates with at least one stop element (11) of the anchoring device (1). In one method of implementation, particularly visible in FIGS. 1A and 1D, the stop element (11) includes a projecting lug on at least one face of the anchoring device (1). In the example shown, this stop element consists simply of a lug orientated toward the interior of the circle of which the arc described by the body (10) forms part, but the lug may adopt different orientations. The cage (2A, 2B) or the prosthesis (2C) may then simply include, below the slot (20), a contact surface for this stop element (11). The stop element surface (21) of the cage (2A, 2B) or of the prosthesis (2C) may then include a peripheral surface of the wall (25) or of the plate (51, 52) to accommodate this projecting lug on at least one face of the body (10) of the anchoring device (1). In another method of implementation that is particularly visible in FIGS. 1B and 1C, the stop element (11) includes two projecting lugs on the sides of the body (10). These two lugs may consist of two latches click-fitted in the slot. In this method of implementation, the stop element surface (21) of the cage (2A, 2B) or of the prosthesis (2C) may include, for example, two recesses (21) located on either side of the slot (20) to accommodate two projecting lugs on the sides of the body (10) of the anchoring device (1). These two recesses may, for example, have a shape and dimensions to suit the click-fitting of the lugs of the anchoring device (1). In addition, as may be seen particularly in FIGS. 11A and 11C, the periphery of the plates form an opening at the level of the slot for the insertion of the device and the edge located between this opening and the periphery of the plate forms a sort of rod onto which the stop element (11) of the anchoring device (1) may fit. Thus, the stop element (11) of the device (1) may consist of a curved portion that click-fits on the edge of the plate. Thus, the device (1) may be removable (in many methods of implementation) and may be implanted in the vertebrae and fitted onto the plates of the prosthesis after the implantation of the latter between the vertebrae. This method of implementation allows adjustment, where appropriate, of the position of the prosthesis between the vertebrae before definitive securing.

In certain methods of implementation of the invention, the body (10) includes, on at least one of its sides, one or more flexible lugs (14) orientated toward the abutment end and forming a stop element to oppose the withdrawal of the anchoring device (1). As may be seen particularly in FIGS. 1A and 1B, this flexible lug (14) may be present on the two lateral sides of the body (10), but it may naturally be located on a single face of the body, such as the top or bottom face, for example. This (or these) flexible lug(s) (14) are used to secure the anchoring device (1) in relation to the cage (2A, 2B) or the prosthesis (2C), by means of their orientation in the direction of the abutment end. When the device (1) is inserted into the slot (20), the lugs (14) fold up because of their flexibility, thus allowing the passage of the device (1) in the slot even if the width of the body (10) is substantially the same as the length of the slot (20), as mentioned previously, as a result, for example, of the recesses in the body (10) provided for the folding over of these lugs (14) or by means of the shape of the body (10) in relation to the slot (20). The position of these flexible lugs (14) on the body (10) may also be arranged so that they emerge at the other side of the slot (20), along the bottom or top surface of the wall (25) of the cage (2A, 2B) or at the bottom or top surface of the plate (51, 52) of the prosthesis (2C). In this method of implementation, at the bottom or top surface of the wall (25), the slot (20) may include at least one stop element surface that mates with these lugs. On the other hand, the position of these flexible lugs (14) on the body (10) may also be arranged so that they do not emerge from the slot (20), which may then have at least one recess allowing the lugs (14) to unfold and oppose the withdrawal of the anchoring device (1).

In certain methods of implementation of the invention, the body (10) is equipped with notches (12) that are orientated so as to oppose the withdrawal of the device (1) after it has been implanted in a vertebra. As may be seen particularly in FIGS. 1A and 1B, the number, the dimension and the shape of these notches (12) may vary according to the implementation variants, without moving outside the spirit of the invention.

Depending on the methods of implementation, the cage (2A, 2B) may have different shapes. The description that follows gives some non-limiting implementation variants with reference to the appended Figures, but the cage (2A, 2B) and the prosthesis (2C) may of course have other shapes without moving outside the spirit of the invention. For example, the cage (2A) represented in FIG. 2 (A to E) is substantially annular, with a periphery that is substantially circular, except at the location of the slot (20) for insertion of the anchoring device (1), at which point it will be held by an implantation instrument (3, 4). The shape of the cage (2A, 2B) or of the prosthesis (2C) may vary, of course, and the shape of the end of the said instrument (3, 4) in contact with the cage (2A, 2B) or the prosthesis (2C) may vary as a consequence, according to some of the methods of implementation. The cage (2A, 2B) and the prosthesis (2C) may, for example, have different shapes, which preferably have a slot (20) designed for the insertion of the device (1), and attachment resources (24) adapted to mate with one end of an implantation instrument. Depending on the methods of implementation, these attachment resources (24) may be associated with a particular shape of the cage (2A, 2B) or of the prosthesis (2C) close to these attachment resources (24) to allow a good fit with the instrument or may even have such particular shapes fitting onto complementary shapes of the instrument. For example, the instrument may include a contact surface fitting closely onto the shape of the prosthesis (2C) close to the recess (24) and/or of the slot (20). Likewise, as mentioned previously, the cage (2A, 2B) may include a cavity (23) at its centre or not, to the extent that it is common to implant several intersomatic cages (2A, 2B) in a given intervertebral space (on condition that the dimensions allow it). The cages thus implanted are generally used to enclose bony tissue (a graft) which will grow within the intervertebral space and allow a fusion (arthrodesis) of the two vertebrae between which it is implanted. It is also common to use a substitute instead of an osseous graft. In any event, the aim of the cage (2A, 2B) is to restore or maintain a space between the vertebrae. Before the growth of the graft and the fusion of the vertebrae, the cage (2A, 2B) should remain correctly in position in the disc space, and various embodiments of this present invention facilitate its immobilisation.

Before the implantation of the anchoring device (1) used to maintain the cage (2A, 2B) in position, there may be a risk that the cage (2A, 2B) will move within the disc space. In certain methods of implementation, at least one of the top and bottom surfaces of the wall (25) will include notches (22) that prevent movement of the cage (2A, 2B) between the vertebrae between which it is implanted. Likewise, at least one of the plates (51, 52) of the prosthesis (2C) may be fitted, on its surface in contact with the vertebrae, with stabilisation resources, such as notches or fins or any type of structure that may be used to prevent its movement between the vertebrae, so as to enhance stability of the prosthesis before it is secured by the anchoring device (1). Thus, at least one of the top and bottom surfaces of at least one of the plates (51, 52) may include notches (22) that prevent movement of the prosthesis (2C) between the vertebrae between which it is implanted. According to various methods of implementation, these notches (22) or other stabilisation resources may have different orientations, so as to prevent movement of the cage (2A, 2B) or of the prosthesis (2C) in one or more directions. For example, the notches (22) may be substantially parallel to each other and all orientated perpendicularly to the axis of insertion of the cage (2A, 2B) or of the prosthesis (2C), but on the other hand the notches (22) may have different orientations on different portions of the cage (2A, 2B) or of the prosthesis (2C), so as to prevent movement in any direction.

In some situations, in particular depending on the vertebrae between which the cage (2A, 2B) or the prosthesis (2C) must be implanted, it is desirable that the cage (2A, 2B) or the prosthesis (2C) allow the imposition of a lordosis or kyphosis in addition to maintaining the space between the vertebrae. Certain methods of implementation therefore provide that the mean planes passing along the top and bottom surfaces of the cage (2A, 2B) form an angle (A1) that imposes a lordosis on the vertebrae between which the cage (2A, 2B) is implanted. For example, FIG. 2B represents a view from above of a cage (2A) according to one method of implementation of the invention. This cage is implanted substantially along axis 2C-2C representing, in FIG. 2B, the plane of the view in section of FIG. 2C. FIG. 2C shows that the mean planes (28) of the bottom and top surfaces of the cage (2A) form an angle (A1) which imposes a lordosis along axis 2C-2C. On the other hand, in certain methods of implementation, the mean planes passing along the top and bottom surfaces of the cage (2A, 2B) may be substantially parallel to each other. Likewise, the prostheses (2C) may include plates whose top and bottom surfaces are substantially parallel to each other but may include plates whose top and bottom surfaces form an angle that may, for example, impose a lordosis or a kyphosis. Thus, in certain methods of implementation, the mean plane passing along the top and bottom surface of at least one of the plates (51, 52) of the prosthesis (2C) forms an angle (A1) that imposes a lordosis on the vertebrae between which the prosthesis (2C) is implanted, for example as described in U.S. patent application Ser. No. 11/109,276 or U.S. patent application Ser. No. 11/098,266, each of which is incorporated herein by reference. In other methods of implementation, the mean planes passing along the top and bottom surfaces of at least one of the plates (51, 52) of the prosthesis (2C) are substantially parallel to each other. In the case of prostheses that include a mobile central core (53) whose movement is limited by mating resources (530), the lordosis may be obtained by a core (53) that at rest is moved off-centre by means of these mating resources (530) and/or the mating resources (531) of the plate.

In addition, in certain methods of implementation, the peripheral wall (25) of the cage (2A, 2B) may include at least one chamfer (250) on at least one peripheral portion of at least one of its top and bottom surfaces, so as to facilitate the insertion of the cage (2A, 2B) between the vertebrae. As may be seen particularly in FIG. 2B, this chamfer (250) of the cage (2A) may be located substantially in the axis (2C-2C, FIG. 2B) of implantation of the prosthesis. In addition, as may be seen particularly in FIG. 2D, this chamfer (250) may be present on the two bottom and top surfaces of the cage (2A). This chamfer (250) or bevelled profile facilitates the implantation of the cage (2A, 2B) by according it a height that is somewhat less on its attacking edge (that is inserted first) than on the rest of the cage. Likewise, the plates of the prosthesis (2C) may include, on the periphery of their surface in contact with the vertebrae, at least one chamfer to facilitate the insertion of the prosthesis (2C) in the disc space.

In certain methods of implementation, the peripheral wall (25) of the cage (2A, 2B) includes two superimposed slots (20) each of which is orientated toward one of the top and bottom surfaces, so as to allow anchoring of the anchoring device (1) in each of the vertebrae between which the cage (2A, 2B) is implanted. Likewise, each of the plates (51, 52) may include a slot (20), each of which may be orientated toward one of the top and bottom surfaces, so as to allow the securing of each of the plates (51, 52) by the anchoring of an anchoring device (1) in each of the vertebrae between which the prosthesis (2C) is implanted. In other methods of implementation, the cage (2A, 2B) may have only single slot (20). In some embodiments, only one plate (51, 52) of the prosthesis (2C) has a slot and the other plate has none.

In certain methods of implementation, the cage (2A, 2B) may be implantable on an axis located substantially along the plane of the intervertebral space but which is oblique in relation to the vertical axis of the vertebral column so as, for example, to allow the implantation between the vertebrae at the point at which blood vessels pass, preventing frontal access to the intervertebral space. In this case, the cage (2A) should be implanted on an axis of implantation that is oblique in relation to the antero-posterior axis of the vertebral column (the sagittal axis) meaning the axis in which a lordosis may have to be imposed. As shown in FIG. 3B, the axis of insertion of the anchoring device (1) is orientated along axis 3C-3C, representing the section plane of FIG. 3C and the cage (2A) is implanted on this axis, but because of the possible dimensions of the access to the intervertebral space, the antero-posterior axis of the vertebrae may be orientated along axis 3D-3D in relation to the cage, which may thus be implanted obliquely. As may be seen particularly in FIG. 3A, and by comparison with FIGS. 3C and 3D, cage (2A) may allow the imposition of a lordosis by means of an angle (A1, FIG. 3A) of inclination between its top and bottom surfaces, but the axis of inclination of the mean planes (28) passing along its top and bottom surfaces is orientated along axis 3D-3D and not along axis 3C-3C. The cage therefore imposes a larger lordosis along axis 3D-3D than along axis 3C-3C in order that it may be implanted along oblique axis 3C-3C in relation to axis 3D-3D corresponding to the antero-posterior axis of the vertebrae (the sagittal axis). Thus, a cage according to this particular method of implementation may be implanted obliquely and allow the imposition of a lordosis that is aligned correctly with respect to the vertebral column.

In other methods of implementation, the peripheral wall (25) may include at least two slots (20) located alongside each other, with each of these defining one possible axis of insertion of the anchoring device (1) in the cage (2A, 2B) and, indirectly, one possible axis of insertion of the cage (2A, 2B) between the vertebrae. For example, as may be seen particularly in FIGS. 4A and 4B, the cage (2A) includes 2 superimposed slots (20) each of which is orientated toward one of the top and bottom surfaces of the cage on a first axis (4C-4C, FIG. 4B) located alongside 2 superimposed slots (20) each of which is orientated toward one of the top and bottom surfaces of the cage on a second axis (4D-4D, FIG. 4B). In this implementation variant, the cage (2A) may be implanted along axis 4C-4C or along axis 4D-4D but the inclination of the mean planes passing along the top and bottom surfaces of the cage is orientated along axis 4C-4C, as may be seen by comparison with FIGS. 4C and 4D. This type of cage may therefore be implanted obliquely (along axis 4D-4D) or frontally (along axis 4C-4C). In a relatively similar manner, the plates (51, 52) of the prostheses represented in FIGS. 11A to 11D include several slots (20) each. In the examples shown, these slots are located on the edges of the plates, but either centred in relation to the antero-posterior axis of the prosthesis, or moved off-centre. These slots then define two possible axes of insertion of the osseous anchoring device (1), namely either on the anteroposterior axis, or on an oblique axis. In addition, the attachment resources (24) of the prosthesis (2C) are located close to each of these slots, so as to allow gripping of the prosthesis during the impacting of the device (1) in the vertebrae. Thus, these attachment resources (24) also define two possible axes of insertion of the prosthesis (2C) between the vertebrae by the instrument, namely either an anteroposterior axis, or an oblique axis. After appreciating this disclosure, those of skill in the art will appreciate that the invention allows many variants regarding the position and the shape of these attachment resources (24) and of the slots (20). It will be noted in passing that in FIGS. 11A and 11B, for example, the devices (1) of the two anchoring plates do not have the same orientation as each other, which may be explained by a different orientation of their slot (20). Naturally, these Figures are simply illustrative, and in no way limiting, since it is possible to envisage any type of combination of orientations and of shapes and of position slots (20) on the plates after appreciating this disclosure.

In other methods of implementation, the intersomatic cage may be of the transforaminal type, meaning implanted through the foramen. This type of cage, which is described, for example, in patent application FR 06 01315 and U.S. patent application Ser. No. 11,378,165 each submitted by the present applicant and which are incorporated herein by reference, is particularly advantageous because it is relatively small and may therefore be implanted by the transforaminal route. In various methods of implementation of this present invention, the cage (2B) is in the shape of a circular arc, as may be seen particularly in FIGS. 8A and 8B, and includes at least one slot (20) of shape, dimension and orientation to suit the insertion of a curved anchoring device (1) according to the different methods of implementation of this present invention. As may be seen particularly in FIG. 8A, the wall (25) of the cage may form a cavity (23), internal or not, as for the cages (2A) described previously. In addition, as may be seen particularly in FIG. 8A, the wall (25) may include at least one lateral opening (26) that allows the growth of the graft through the cage (2B). Although these lateral openings have not been represented in the other Figures with reference to the cages (2A) described previously, after appreciating this disclosure those of skill in the art will recognize that these too may also include such openings (26), where appropriate. This type of cage (2B) has an arcuate peripheral wall (25), for example describing a circular arc. The radius of curvature of the cage (2B) and the dimensions of the latter may naturally vary according to the methods of implementation, and according to the vertebrae between which they must be implanted. The wall (25) in an arc of the cage (2B) is extended, at one of its ends, by a return part extending in the direction of the inside of the curve described by the wall (25). In certain methods of implementation, as may be seen particularly in FIGS. 8B and 8C, this return part may include a chamfer (250) to facilitate its implantation between the vertebrae. Like for the first implementation variants of intersomatic cages (2A), these transforaminal implementation variants of the intersomatic cages (2B) may be equipped with notches (22) on at least one part of at least one of their bottom or top surfaces. Whatever the type of cage (2A, 2B), these notches (22) may have different orientations and present a pattern that is linear or circular, or any other type of pattern, and the lines or circles described by the notches may either cross each other or not. For example, as may be seen particularly in FIGS. 8B and 8C, the notches (22) may describe a pattern of chevrons or of circular arcs. The different methods of implementation of the anchoring device (1) described previously with reference to the previous methods of implementation of intersomatic cages (2A) may naturally be adapted to these transforaminal implementation variants of the cage (2B) and vice versa. Likewise, the different methods of implementation concerning the slots (20) may be adapted to this type of transforaminal cage (2B) and vice versa, on condition that the dimensions allow it or are adapted to allow it.

In some methods of implementation, the intersomatic cages (2A, 2B) or the intervertebral prostheses (2C) will be implanted by means of a special instrument (3, 4) that is used to implant them between the vertebrae and that may be used to implant the anchoring devices (1) in the vertebral plates. In these methods of implementation, the peripheral wall (25) of the cages (2A, 2B) or at least one of the plates (51, 52) may include at least one attachment resource (24) that mates with a gripper end of an instrument (3, 4) for implantation of the cage (2A, 2B) or of the prosthesis (2C). As mentioned previously, this attachment resource (24) may include at least one recess (24) that receives the end of a gripping resource (321). As may be seen particularly in FIG. 3A, the cage may include two recesses (24) each located on one side of the slot, to facilitate gripping of the cage, but the recesses of course may be located in other places, preferably for these recesses to facilitate the gripping of the cage (2A, 2B) or of the prosthesis (2C) by a complementary instrument. As may be seen particularly in FIG. 4A, a slot (20) in the cage may be associated with a single recess (24) but it is possible to provide several recesses (24) around the slots (20), even when the cage (2A, 2B) includes several slots (20) as in this implementation example. These different variants concerning the number and the position of the attachment resources (24) and of the slot (20) described here naturally apply equally well to the cages (2A, 2B) and to the prostheses (2C).

Various embodiments of the present invention therefore also concern an instrument (3, 4) for the implantation of an intersomatic cage (2A, 2B) or of an intervertebral disc prosthesis (2C) between the vertebrae and for the implantation of an anchoring device (1) in at least one of these vertebrae. The instrument may include an impactor (4) that includes a head (40) whose shape and dimensions are designed to push on the anchoring device (1). The instrument may also include a guide (3) of elongated shape on a longitudinal axis extending between a first end, called the gripping end of the cage or of the prosthesis, and a second end, called the push end. The gripping end includes at least one gripping resource (321) that mates with at least one means (24) of attaching the cage (2A, 2B) or the prosthesis (2C). Depending on the methods of implementation, the push end may include a handle (33) that is used to push the guide holding the cage (2A, 2B) or the prosthesis (2C) in order to insert the latter into the intervertebral space. This handle may also consist of a stop element on which the surgeon may tap, by means of a tool of known type for example, in order to introduce the cage or the prosthesis between the vertebrae. After appreciating this disclosure those of skill in the art will recognize that the different elements of the instrument (3, 4) described here may be present whatever the method of implementation of the cage (2A, 2B) or of the prosthesis (2C), unless it is expressly specified in this present description that a particular element concerns only one type of cage described previously or a single type of prosthesis.

The guide (3) of the instrument may include a head (30) whose shape and dimensions are designed to at least partially accommodate the head (40) of the impactor, and includes at least one guidance surface (31) having a radius of curvature that is substantially the same as the radius of curvature of the anchoring device (1). This curved surface (31) may guide this anchoring device (1) through the slot (20) of an intersomatic cage (2A, 2B) or of an intervertebral prosthesis (2C), for the impacting of the anchoring device (1) into a vertebral plate of one of the vertebrae between which the cage (2A, 2B) or the prosthesis (2C) is implanted.

The guide (3) may include an elongated body (32) that allows an approach to the intervertebral space without needing a lot of space. The impactor (4) also may include an elongated body (42), which slides in relation to the body (32) of the guide (3). In certain methods of implementation, the impactor (4) includes a handle (41) which is used to cause the body (42) of the impactor to slide in relation to the guide (3). This handle may also play the role of a stop element on which the surgeon may tap, by means of a tool of known type for example, in order to cause the anchoring device (1) to penetrate into a vertebral plate. In addition, in certain methods of implementation, the impactor (4) may include at least one stop element (43) which limits the penetration of the head (40) of the impactor (4) within the head (30) of the guide (3). In certain variants, the position of this stop element may be adjustable along the body (42) of the impactor (4), for use in adjusting the penetration of the impactor to the size of the head (30) of the guide (3) and to the size of the anchoring device (1) employed. For example, as mentioned previously, the anchoring device (1) may have a length that is variable to suit the circumstances and the head (30) of the guide, and in particular the curved guidance surface (31) will also be of a size designed for this length of the anchoring device (1).

Depending on the methods of implementation, the body (32) of the guide (3) may have two rods or tubes (32), as shown in FIG. 6B, but the guide (3) may have a single rod or a single tube, even if the guide includes several gripping resources (321), preferably allowing these resources (321) to secure the cage or the prosthesis. As may be seen particularly in FIG. 6D, in certain methods of implementation, the gripping resources (321) may consist of rods (321) fitted freely within the tubes (32) constituting the body of the guide (3). In some embodiments, these rods may not be within the body (32). In different methods of implementation, the gripping resource (321) may comprise one end of a rod which slides in a body (32) of the guide (3) when it is operated by a handle (33) so as to enter and leave the recess (24) of the cage (2A). In these implementation variants, these gripping resources (321) may include threads at their ends so as to be screwed within the recess (24) of the cage (2A, 2B), which may include a tapping. In certain implementation variants, the rod (321) may therefore include a threaded end fitting into a tapping in the recess (24) in order to secure the cage (2A) when the rod is operated by the handle (33). In other variants, the rod may have dimensions that are adjusted to penetrate exactly into the recess, and allow the retention of the cage by this exact adjustment. These different variants of the rod (321) and of the recess (24) naturally may also be applied to prostheses (2C). For example, the prostheses represented in FIGS. 11A to 11D include plates (51, 52) that include recesses (24) to accommodate these gripping resources (321). In the examples of implementation represented, the gripping resources (321) may be located close to the top and bottom surfaces of the head (30) of the guide (3) so that these resources (321) allow the correct gripping of two plates (51, 52) of the prosthesis (2C). Various embodiments of the invention allow other methods of implementation of the attachment resources (24) and of the gripping resources (321), for example as mentioned previously. In addition, in the implementation example of the prosthesis (2C) of FIGS. 11C and 11D that includes two plates (51, 52) and a core (53), the attachment resources (24) may also include attachment resources located on the core, so that the latter is also retained by the instrument. For example, the surface of the head (30) of the guide facing the prosthesis (2C) may have a shape that is complementary to the two plates and to the core assembly, so as to hug the shape of the prosthesis and keep the elements of the prosthesis stable.

In the methods of implementation represented in FIGS. 6 (A to E) and 7 (A to D), the body (32) includes a guidance plate (34) that is used to guide the impactor (4). In these methods of implementation, the plate (34) includes a groove that guides the impactor on the axis of the body (32) of the guide. In other possible methods of implementation, as represented in FIG. 9A, for example, the body (42) of the impactor (4) may be mounted to slide within the body (32) of the guide, but the invention naturally allows other implementation variants, preferably allowing the impactor (4) to be guided in relation to the head (30) and to slide in relation to the guide (3).

As may be seen particularly in FIG. 5A, the head (30) of the guide (3) includes a cavity (300) whose shape and dimensions are designed to receive the anchoring device (1) and, at least partially, the head (40) of the impactor (4). Various embodiments of the invention naturally allow different methods of implementation of the head (30) and the examples given here are only by way of illustration. The head (30) of the guide may include at least one passage (320) through which the gripping resource (321) of the cage or of the prosthesis will be inserted in order to hold the cage or the prosthesis at the end of the guide (3). In the method of implementation represented in FIGS. 5A and 5B, this head includes two identical passages on either side of the cavity (300), since this method of implementation of the head (30) is designed to be mounted on a guide (3) that has two gripping resources (321). After appreciating this disclosure those of skill in the art will recognize that the invention will allow the use of only one gripping resource (321) or, on the other hand, an increase in their number by reducing their size and by distributing them differently around the cavity, for example, with the provision of complementary recesses on the cages to be implanted. In addition, a given instrument (3, 4) may serve for the implantation of different types of cages (2A, 2B) or prostheses (2C), preferably with the gripping resources (321) of the guide (3) and the attachment resources (24) of the cages (2A, 2B) or of the prostheses (2C) being designed to be complementary. For example, the instrument that includes a head (30) as represented in FIG. 5E, may serve for the implantation of the cage (2A) of FIG. 4A, even though one of the gripping resources (321) of the guide (3) will not be used in this case. Inside the cavity (300) of the head (30) of the guide (3) there may be at least one curved guidance surface (31) of the anchoring device (1). In the methods of implementation illustrated here by way of example, this guidance surface (31) may include at least two curved grooves (31) each located on either side of this cavity (300) to guide the anchoring device (1) on both sides of its body (10). The head (40) of the impactor (4) is then designed to penetrate into the cavity (300) from one end to the other of these grooves (31), so as to push the anchoring device (1) from one end to the other of these grooves (31). In the method of implementation represented in FIG. 5 (A to E), the cavity (300) of the head (30) may receive two guidance elements (310) (particularly visible in FIGS. 5C and 5D), with each including the guidance grooves (31) and each located on one side of the cavity (300), as may be seen particularly in FIG. 5E. In this implementation example, the guidance elements (310) are assembled with the head (30) by inserting it into the cavity (300) which may include securing resources that are used to immobilise these guidance elements (310). In other examples of implementation such as, for example, the head (30) of the guide (3) represented in FIGS. 8C and 9 (A to C), the head (30) will be made with of the guidance grooves (31) directly on the inside of the cavity (300). In this case, the head may be made in two assembled parts in order to facilitate the machining of the curved grooves (31).

In certain methods of implementation, as shown in FIGS. 3A, 4A and 5A, the recess (24) of the cages (2A) may be created close to the slot (20), and the passage (320) for the gripping resources (321) may be close to the cavity (300) so as to allow correct gripping of the cage close to the site at which the anchoring device (1) is likely to apply pressure on the cage under the action of the impactor (4). The resource (24) for attachment of the prostheses (2C) may naturally be made in the same way.

As may be seen particularly in FIGS. 6C and 9B, the gripping resource (321) may protrude beyond the head (30) of the guide (3) at the position of the gripping end. As may be seen particularly in FIGS. 7A and 7B or in FIGS. 9A and 9C, the guide may allow the gripping of the cage (2A, 2B) with one end of the guidance surface (31) ending in the slot (20) in the cage (2A, 2B) thus held, and the other end of the guidance surface (31) remaining accessible for the insertion of the anchoring device (1). In these methods of implementation, the anchoring device (1) may be inserted in the head (30) after the cage (2A, 2B) has been mounted on the gripping resources (321), but other methods of implementation, which may be less advantageous but less costly to implement, may require insertion of the anchoring device (1) prior to the mounting of the cage (2A, 2B). These variants also may apply to the prostheses (2C) which may be designed in the same way and may therefore be implanted with the same instrument as that described for these cages (2A, 2B).

In the case of the transforaminal cages (2B), the instrument may allow the cage to be held over virtually the whole of its length, which may facilitate the insertion of the cage (2B) into the intervertebral space and protect it from damage. In this method of implementation of the cage (2B), the gripping resource (321) may be the end of a curved rod, such as a spatula, which may have a radius of curvature substantially identical to a radius of curvature of the cage (2B) having a peripheral wall (25) describing an arc. In this method of implementation, the recess (24) may be located on the return part extending one end of the circular arc described by the wall (25) of the cage (2B) in the direction of the centre of the circle of which the circular arc described by the wall (25) forms part. The spatula may hug the shape of the cage (2B) between this return part and the other end of the circular arc described by the wall (25) of the cage (2B). At this other end of the wall (25), the cage (2B) advantageously may include a second gripping resource to hold the cage (2B). In certain methods of implementation of the transforaminal cage, this second gripping resource may be located at the base of the spatula, but on the side opposite to that carrying the spatula. This second gripping resource may include a second recess (241) to accommodate a latch (341) mounted on a rod (340) of the guide (3). As explained previously for the body (32) of the guide and the body (42) of the impactor or the gripping resources (321), this rod (340) may be mounted freely within the body (32) of the guide or on the outside, preferably so that it is guided in relation to the head (30). This rod (340) may be operated by a handle and may pivot between at least one position at which the latch (341) engages the second recess (241), and a position at which the latch (341) exits from the second recess (241) and thus frees the cage (2B).

In certain methods of implementation of the implantation instrument (3, 4), particularly suitable for the transforaminal cages whose insertion must be accomplished along an arc or an oblique axis in relation to the antero-posterior axis of the vertebrae, the head (30) of the guide (3) may be curved or bent substantially along the radius of curvature of the arc described by the cage (2B). Thus, the bent instrument allows easier passage through the foramens, although it may be used in another context. In this bent method of implementation of the head (30) of the guide (3), the head (40) of the impactor (4) may have a shape that is more or less curved or bent so that it has a radius of curvature compatible with its passage in the head (30) of the guide (3). In addition, in a particularly advantageous variant, this head (40) of the impactor (4) may be mounted on an axis (425) of rotation mounted on the body (42) of the impactor. This axis (425) allows the head (40) of the impactor to pivot in order to pass the curvature or the bend in the head (30) of the guide (3), as may be seen particularly in FIG. 9B. In another implementation variant, the impactor (4) may be straight and designed to be inserted in the head (30) on an oblique axis, substantially parallel to axis 9C-9C of FIG. 9B for example, with the head (30) then having an opening of sufficient size to allow the introduction of the head (40) of the impactor (4).

After appreciating this disclosure those of skill in the art will recognize that this present invention allows methods of implementation in many other specific forms without moving outside the scope of the invention. As a consequence, these present methods of implementation must be considered to be illustrations only, but may be modified within the area defined by the scope of the attached claims, and the invention should not be limited to the details given above.

The invention claimed is:

1. A fusion cage system configured for implantation in the intervertebral space between adjacent vertebrae and the fusing of the adjacent vertebrae, the fusion cage system comprising:
   a cage comprising
      a peripheral wall, the peripheral wall comprising a top surface, a bottom surface, and an exterior face disposed between the top surface and the bottom surface, and
      an enclosed channel extending from an opening in the exterior face toward the top surface; and
   an anchor comprising a curved plate having a radius of curvature along a longitudinal axis of the anchor extending from a penetration end of the anchor to an impaction end of the anchor, with the orientation of the penetration end and the orientation of the impaction end forming a fixed angle established by the radius of curvature,
   the anchor being movable between
      a withdrawn position in which the anchor is completely removed from the channel with the fixed angle in a first orientation, and
      an inserted position in which the anchor is inserted in the channel with the penetration end projecting above the top surface, a portion of the curved plate extending through the channel, the impaction end disposed adjacent to the opening in the exterior face, and the fixed angle remaining constant but rotated to a second orientation.

2. The fusion cage system of claim 1 in which the anchor comprises a lug projecting from the side of the plate and the channel comprises a recess disposed along the exterior face sized to accept the lug with the anchor in the inserted position.

3. The fusion cage system of claim 1 in which the anchor comprises a flexible lock projecting from the side of the plate and the channel comprises a receptacle sized to admit a projecting end of the lock, with the lock movable between a compressed position in which the anchor is removable from the channel and an extended position in which the lock is disposed in the receptacle and the anchor is locked in the inserted position in the channel.

4. The fusion cage system of claim 3 in which the anchor comprises a lug projecting from the side of the plate and the channel comprises a recess disposed along the exterior face sized to accept the lug with the anchor in the inserted position.

5. The fusion cage system of claim 4 in which the plate comprises notches orientated to oppose withdrawal of the anchor from a vertebra after the penetration end is driven into the vertebra.

6. The fusion cage system of claim 4 in which the anchor is movable between the withdrawn position to the inserted position in an insertion direction, and the top surface of the peripheral wall comprises an array of linear grooves oriented angularly to the insertion direction.

7. The fusion cage system of claim 6 in which a cavity of the cage comprises an interior face and a brace that traverses the cavity from a first point on the interior face to a second point on the interior face.

8. The fusion cage system of claim 7 in which the brace comprises a top surface extending the top surface of the peripheral wall across the cavity, and in which the top surface of the brace comprises array of linear grooves oriented in the same direction as the array of linear grooves disposed on the top surface of the peripheral wall.

9. The fusion cage system of claim 1 in which a leading edge of the penetration end is bifurcated by a notch.

10. The fusion cage system of claim 1 in which the radius of curvature is constant along the longitudinal axis.

11. The fusion cage system of claim 1 in which the radius of curvature differs at different points along the longitudinal axis.

12. A fusion device configured for implantation in the intervertebral space between adjacent vertebrae and the fusing of the adjacent vertebrae, the fusion device comprising:
a fusion cage comprising
a peripheral wall, the peripheral wall comprising a top surface, a bottom surface, and an exterior face disposed between the top surface and the bottom surface,
a first passage extending from a first opening in the exterior face toward the top surface, and
a second passage extending from a second opening in the exterior face toward the bottom surface; and
a first anchor and a second anchor separate from and independently movable with respect to the first anchor, each of the first and second anchors comprising a curved plate having a radius of curvature along a longitudinal axis of the anchor extending from a leading end of the anchor to a trailing end of the anchor, with the orientation of the leading end and the orientation of the trailing end forming a fixed angle established by the radius of curvature,
with the first anchor being movable between
a first withdrawn position in which the fixed angle of the first anchor is disposed in a first withdrawn orientation and the leading end of the first anchor does not extend above the top surface, and
a first inserted position in which the first anchor is inserted in the first passage with the leading end of the first anchor projecting above the top surface, a portion of the curved plate of the first anchor extending through the first passage, the trailing end of the first anchor disposed adjacent to the first opening in the exterior face, and the fixed angle of the first anchor remaining constant but rotated to a first inserted orientation that is angularly offset to the first withdrawn orientation, and
with the second anchor being movable between
a second withdrawn position in which the fixed angle of the second anchor is disposed in a second withdrawn orientation and the leading end of the second anchor does not extend above the bottom surface, and
a second inserted position in which the second anchor is inserted in the second passage with the leading end of the second anchor projecting below the bottom surface, a portion of the curved plate of the second anchor extending through the second passage, the trailing end of the second anchor disposed adjacent to the second opening in the exterior face, and the fixed angle of the second anchor remaining constant but rotated to a second inserted orientation that is angularly offset to the second withdrawn orientation.

13. The fusion device of claim 12 in which the first anchor comprises a first lug projecting from the trailing end of the first plate and the first passage comprises a recess disposed along the exterior face sized to accept the lug with the first anchor in the first inserted position.

14. The fusion device of claim 13 in which the first anchor comprises a second lug projecting from a side of the first anchor.

15. The fusion device of claim 12 in which the radius of curvature of the first anchor is constant along the longitudinal axis of the first anchor.

16. The fusion device of claim 12 in which the radius of curvature of the first anchor differs at different points along the longitudinal axis of the first anchor.

17. A spinal treatment device comprising:
a cage configured for fusible implantation in a gap between a first vertebra and a second vertebra, the cage comprising plural vertebral contact surfaces and a passage extending from an opening on a side of the cage toward a first one of the vertebral contact surfaces of the cage; and
an anchor elongated between first and second ends disposed at opposite ends of the anchor, with the anchor formed as a curved plate extending between the first and second ends and having a fixed angle established by the angular orientation of the first and second ends, the anchor being disposable through the passage and having a withdrawn position in which the fixed angle has a first orientation and an inserted position in which the fixed angle has a second orientation with the first end of the anchor disposed outside the passage adjacent to the first one of the vertebral contact surfaces of the cage and the second end of the anchor disposed proximal to the opening on the side of the cage.

18. The spinal treatment device of claim 16 in which the curved plate has a radius of curvature that is constant between the first and second ends.

19. The spinal treatment device of claim 16 in which the curved plate has a radius of curvature that varies between the first and second ends.

20. The spinal treatment device of claim 16 in which the passage extends linearly from the opening toward the adjacent vertebral contact surface.

21. The spinal treatment device of claim 16 in which the passage extends curvilinearly from the opening toward the adjacent vertebral contact surface.

* * * * *